US011167065B2

(12) United States Patent
Orlowski

(10) Patent No.: US 11,167,065 B2
(45) Date of Patent: Nov. 9, 2021

(54) SHELLAC AND PACLITAXEL COATED CATHETER BALLOONS

(71) Applicant: EUROCOR TECH GMBH, Bonn (DE)

(72) Inventor: Michael Orlowski, Bonn (DE)

(73) Assignee: EUROCOR TECH GMBH, Bonn (DE)

(*) Notice: Subject to any disclaimer, the term of this patent is extended or adjusted under 35 U.S.C. 154(b) by 0 days.

(21) Appl. No.: 16/411,801

(22) Filed: May 14, 2019

(65) Prior Publication Data
US 2019/0275211 A1 Sep. 12, 2019

Related U.S. Application Data

(62) Division of application No. 13/266,059, filed as application No. PCT/EP2010/002824 on Apr. 26, 2010, now Pat. No. 10,293,085.

(30) Foreign Application Priority Data

Apr. 24, 2009 (EP) ..................................... 09075191

(51) Int. Cl.
*A61L 29/16* (2006.01)
*A61M 25/10* (2013.01)
*A61L 29/08* (2006.01)

(52) U.S. Cl.
CPC ............ *A61L 29/16* (2013.01); *A61L 29/085* (2013.01); *A61L 2300/416* (2013.01); *A61L 2300/606* (2013.01); *A61L 2420/02* (2013.01)

(58) Field of Classification Search
CPC ........................................................ A61L 29/16
See application file for complete search history.

(56) References Cited

U.S. PATENT DOCUMENTS

2009/0227948 A1* 9/2009 Chen ..................... A61L 29/085
604/103.02

FOREIGN PATENT DOCUMENTS

| EP | 1916006 | * 10/2006 |
| WO | WO 2008/089730 | * 1/2008 |
| WO | WO 2009/144541 | * 3/2009 |

* cited by examiner

*Primary Examiner* — Sarah Alawadi
(74) *Attorney, Agent, or Firm* — Schroeder Intellectual Property Law Group, LLC

(57) ABSTRACT

The present invention relates to a method for coating catheter balloons with the pharmacological agent paclitaxel and the biological and biodegradable polymer composition shellac and optionally further components. Moreover the present invention relates to paclitaxel and shellac coated catheter balloons obtained according to the coating methods disclosed herein as well as the use of such coated catheter balloons for the short time release of the pharmaceutically active agent paclitaxel for prophylaxis and treatment of restenosis especially restenosis caused by angioplasty. The coated catheter balloons can be used alone or in combination with a coated or uncoated stent crimped on the catheter balloon before or after the coating with shellac and paclitaxel.

13 Claims, 5 Drawing Sheets

Fig. 2
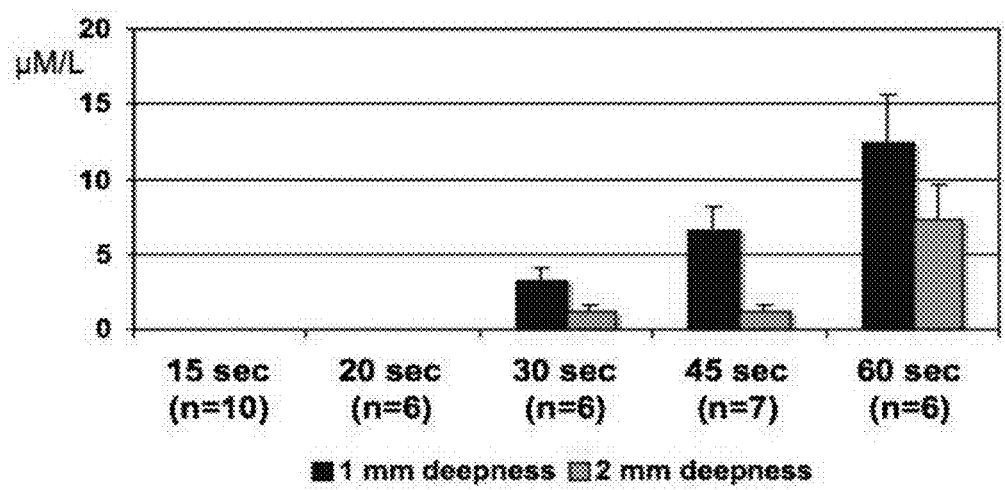
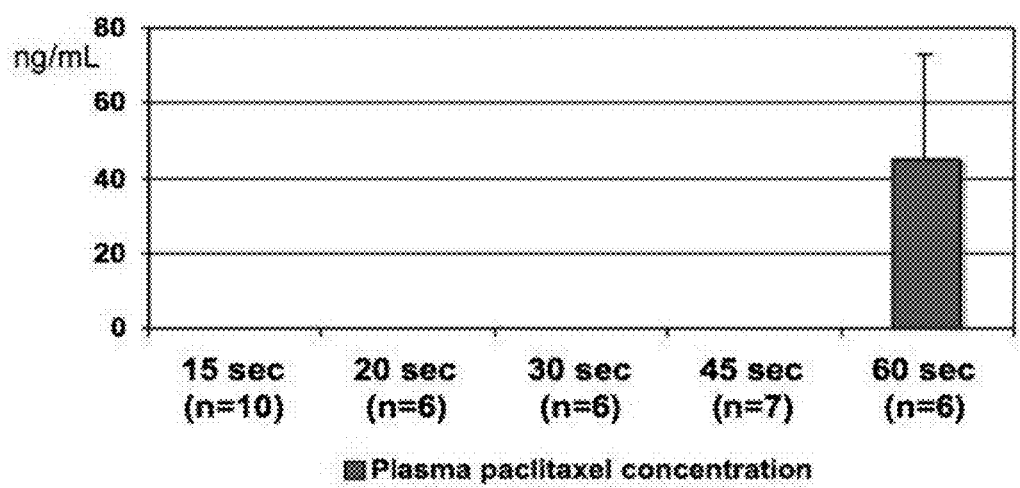

Fig. 3

| | DIOR paclitaxel-shellack balloon (n=6) | AMADEUS Supercross uncoated balloon (n=6) | p value |
|---|---|---|---|
| Histopathologic parameter | | | |
| Injury score | 1.00±0.89 | 0.83±0.75 | 0.734 |
| Fibrin score | 0.50±0.55 | 0.33±0.52 | 0.599 |
| Inflammation score | 0.17±0.41 | 0.50±0.84 | 0.401 |
| Endothalialization complete | 6/6 (100%) | 6/6 (100%) | 1.0 |
| Histomorphometric parameter | | | |
| Lumen area (mm$^2$) | 1.20±0.27 | 0.59±0.22 | <0.001 |
| Neointimal area (mm$^2$) | 0.19±0.04 | 0.70±0.66 | 0.045 |
| Internal elastic lamina area (mm$^2$) | 1.39±0.26 | 1.28±0.72 | 0.366 |
| Media area (mm$^2$) | 1.14±0.35 | 1.10±0.59 | 0.443 |
| External elastic lamina area (mm$^2$) | 2.50±0.55 | 2.38±1.24 | 0.417 |
| % Area stenosis (%) | 14.44±3.80 | 44.81±22.93 | 0.005 |
| Maximal neointimal thickness (mm) | 0.13±0.06 | 0.29±0.19 | 0.039 |
| Vessel remodeling index | 0.86±0.14 | 0.86±0.16 | 0.977 |

Fig. 5

|  | DIOR Paclitaxel-DMSO | DIOR Paclitaxel-shellac |
|---|---|---|
| Drug Load | 3 µg/mm² | 3 µg/mm² |
| Physical Coating | Paclitaxel | Paclitaxel |
| Technical Coating | DMSO | Shellac |
| Coating Colour | White | Transparent |
| Coating Appearance | Crystaline | Resinous |
| Folding Type | 3-fold | 3-fold |
| Release of drug from balloon surface at 30 s inflation time 60 s inflation time | 20% 25% | 75% 85% |

SHELLAC AND PACLITAXEL COATED CATHETER BALLOONS

The present application is a divisional application of U.S. patent application Ser. No. 13/266,059, which is a § 371 national stage entry of International Application No. PCT/EP2010/002824, filed Apr. 26, 2010, which claims priority to European Application No. 09075191.8, filed Apr. 24, 2009—the contents of all of which are fully incorporated herein by reference.

The present invention relates to a method for coating catheter balloons preferably textured catheter balloons with the pharmacological agent paclitaxel and the biological and biodegradable polymer composition shellac and optionally further components. Moreover the present invention relates to paclitaxel and shellac coated catheter balloons obtained according to the coating methods disclosed herein as well as the use of such coated catheter balloons for the short time release of the pharmaceutically active agent paclitaxel for prophylaxis and treatment of restenosis especially restenosis caused by angioplasty. The coated catheter balloons can be used alone or in combination with a coated or uncoated stent crimped on the catheter balloon before or after the coating with shellac and paclitaxel.

Nowadays, implantation of vessel grafts such as stents has become a well-established surgical intervention for the treatment of stenoses. In this context, so-called restenosis (recurrent stenosis), i.e. the reocclusion of the vessel is a frequently occurring complication. There's no exact definition of the term restenosis to be found in literature. The most frequently used morphological definition of restenosis defines restenosis as a reduction of the vessel diameter to less than 50% of the normal value subsequent to successful PTA (percutaneous transluminal angioplasty). Said definition describes an empirically determined value and its hemodynamic meaning and association with clinical symptoms lack scientific background. In practice, clinical deterioration in a patient is often considered a sign for the occurrence of restenosis in the previously treated vessel section.

Restenosis following stent implantation is one of the major causes for further hospitalization. Vessel traumas induced during stent implantation cause inflammatory reactions which play a decisive role in the healing process during the first seven days. In the recent past, it has also been found that stents provided with a drug-eluting coating may cause late thromboses, i.e. in addition to restenosis the stent may also lead to long-term problems such as late thromboses.

Concerns have been raised that biostable or bioreabsorbable polymeric matrix of the stent, in which the drug is embedded, might induce sustained inflammation with increased neointimal proliferation. Additionally, the tissue drug concentration in the stent area is not homogenous: it is highest near to the stent struts, and lowest between the struts, which causes non-uniform inhibition of smooth muscle cell proliferation and may induce delayed and in-homogenous reendothelization in different stent segments. Both mechanisms have been suggested to contribute significantly to late thrombosis and in-stent restenosis. The problem of late thromboses caused by drug eluting stents like paclitaxel eluting stents have been described as serious problem which can cause death of the patient. In comparison to drug eluting stents which release the drug over a certain period of time, drug coated catheter balloons need to immediately release the drug since dilatation of a catheter balloon cannot take longer than 60 seconds in order to avoid any harm to the patient and might be repeated for two or three times. However even repeating the dilatation in order to obtain three or four or five minutes of over-all dilatation time is still a short time release of the drug in comparison with stents which release the drug over days, weeks or months.

To avoid such problems, a so-called "biological stenting" may be performed using only a coated catheter balloon without any stent, i.e. the vessels are dilated at a constricted site by the dilatation of a coated catheter balloon, wherein, while the catheter balloon is dilated for a short period of time, a sufficient amount of pharmacological agent is transferred to the vessel wall to avoid re-constriction or reocclusion of the vessel due to the dilatation of the vessel and the delivery of active agents.

Such coated catheter balloons are already known from WO 2005/089855 A1 and the international patent application WO 2004/028582 A1 discloses multifold balloons which are coated, especially within the folds, with a composition of a pharmacological agent and a contrast medium. A method for spray coating catheter balloons is described in WO 2004/006976 A1.

We have previously shown (DE 102007003184 A1) that there are measurable Paclitaxel concentrations in the coronary arterial tissue after treatment with Paclitaxel-coated balloon (Paclitaxel in DMSO) dilation of a porcine coronary artery. However, the disadvantage of the prior art coated dilatable catheter balloon is the relatively long inflation time (60 s) needed to achieve a measurable Paclitaxel penetration into the arterial wall. The usually recommended 60 s inflation time can cause prolonged ischemia and arterial injury.

Furthermore, we as well as other research groups have found that the hitherto measured Paclitaxel concentrations in porcine coronary artery after treatment with prior art Paclitaxel coated catheter balloons were not effective in exerting a therapeutic effect on the inhibition of restenosis.

Dr. Cortese of the Ospedale Misericordia di Grosseto (Italy) hold a lecture at the European Association of Percutaneous Cardiovascular Interventions (EuroPCR) in 2009 concerning the clinical PICCOLETO-study (www.europcr.com) where he compared the efficiency of a Paclitaxel coated stent against a Paclitaxel coated catheter balloon without any further additives. The clinical study was aborted after ⅔ of the time because it had already become clear, that the Paclitaxel coated catheter balloon showed no effect compared to the Paclitaxel coated stent in his hands. It has to be made clear that a catheter balloon coated with pure Paclitaxel, i.e. Paclitaxel only without any further compounds or additives such as permeation enhancer, compounds for forming micelles, solubilizers, contrast agents, urea, organic acids, organic acid esters, oligomeric or polymeric substances or the like was obviously not effective to reduce restenosis and was consequently therapeutically not useful.

Bruno Scheller & Ulrich Speck et al., Circulation 2004, 110, 810-814 demonstrated that catheter balloons coated with pure Paclitaxel did not show any therapeutic effect. A therapeutic effect was only achieved when the Paclitaxel was combined with the contrast agent solution ULTRAVIST® ULTRAVIST® is a solution of the contrast agent iopromide. The same observation was made by Cremers et al., Clin. Res. Cardiol., 2008, 97-Suppl.1. They compared the PACCOCATH® catheter balloon coated with Paclitaxel and ULTRAVIST® with the DIOR® $1^{st}$ generation catheter balloon coated with Paclitaxel. The late lumen loss was measured in pigs after treatment with PACCOCATH® or DIOR® $1^{st}$ generation catheter balloon coated with Paclitaxel only against a control group. Treatment with PACCOCATH® lead to a significant reduction of late lumen loss, wherein the group treated with DIOR® catheter balloon showed no significant reduction in late lumen loss in their hands.

Due to the fact that the active agent paclitaxel has proven to be particularly useful in the prevention of restenosis, as can be seen especially in European patent no. EP 0 706 376 B1, while coated stents, however, are disadvantageous with respect to the late thromboses described above, it is an objective of the present invention to apply the active agent paclitaxel onto a catheter balloon in such manner that a coating is created which is easily detached from the balloon and can be effectively transferred to the vessel wall so that a therapeutic effect concerning reduction of restenosis can be achieved.

Said objective is solved by the technical teaching of the independent claims. Further advantageous embodiments of the invention result from the dependent claims, the description, the figures and the examples.

Surprisingly it has been found that a coating method of the following type is especially suited for resolving said objective.

Said method for loading or coating dilatable catheter balloons comprises the following steps:

I) providing an uncoated catheter balloon;
and
IIA) providing a solution of paclitaxel and shellac;
or
IIB) providing a solution of paclitaxel and providing a solution of shellac;
and
   IIIA) coating the surface of the catheter balloon with the solution of paclitaxel and shellac;
   or
IIIB) coating the surface of the catheter balloon with the solution of paclitaxel and subsequently with the solution of shellac or coating the surface of the catheter balloon with the solution of shellac and subsequently with the solution of paclitaxel;
IV) drying the coated catheter balloon.

The invention is furthermore directed to a catheter balloon comprising a coating with Paclitaxel and shellac. The term "uncoated" as used herein refers to a catheter balloon with a smooth or structured or roughened surface without any drug coating, i.e. the balloon surface does not comprise a pharmaceutically active agent and especially no anti-proliferative, anti-angiogenic or anti-restenosis drug and no coating containing an anti-proliferative, anti-angiogenic or anti-restenosis drug.

It was surprisingly found that such a Paclitaxel-shellac-coating is therapeutically highly useful in keeping blood vessels open, in reducing the late lumen loss and in reducing restenosis. In comparison to the catheter balloon coated with pure Paclitaxel (DIOR® $1^{st}$ generation) which is not effective in keeping blood vessels open or in reducing the late lumen loss or in reducing restenosis according to the study of Dr. Cortese, it was very surprising that a combination of Paclitaxel and shellac leads to a highly useful catheter balloon. Thus, the present invention provides a catheter balloon and a catheter balloon comprising a catheter balloon coated with a combination of Paclitaxel and shellac which is even after short dilatation times of 30 seconds therapeutically highly useful in keeping blood vessels open and in reducing the late lumen loss and in reducing restenosis.

It was highly surprising that by using a catheter balloon having a catheter balloon coated with Paclitaxel and shellac effective tissue Paclitaxel concentration were achieved after balloon inflation times of only 30 seconds (s), which causes less arterial injury and is better tolerated by the patients in clinical scenario. After 30 sec the tissue longitudinal/horizontal saturation limit is reached with further, minor increase in tissue drug concentration only in the vertical direction. The inflation time of 30 s with catheter balloons coated with Paclitaxel and shellac is as effective as the inflation time of 60 s or 2×30 s, which is usually recommended for drug eluting balloons. Longer inflation of the balloon leads to undesirable release of the drug into the systemic circulation. Short exposure of Paclitaxel to the arterial wall results in penetration of the drug in both longitudinal and vertical directions. In contrast with drug eluting stents, the drug delivery is rapid and homogenous using drug coated dilatable catheter balloon, reaching the maximal tissue drug concentration at the time of the highest level of procedure-induced local tissue injury, which in turn triggers the restenotic and thrombotic cascade.

WO 2008/046641 discloses coated implants, referring to stents in particular showing in vitro release kinetics of stents coated with 1.0% rapamycin without shellac blend and 1.0% rapamycin/0.5% shellac composite. Shellac had a profound impact on stent-based rapamycin by protracting drug release long-term. Uncoated stents with Rapamycin released the drug more efficiently in contrast to shellac and rapamycin coated stents, which released the drug much slower. Shellac was deemed to be useful to modulate the release kinetics of an implant-based, e.g. stent-based compound to slow the release kinetic (more than 60 days) that is required to prevent in-stent restenosis at 6-9 months follow up.

Such a retardation of drug release is not favourable for a catheter balloon, where it is the main goal, in contrast to a stent, to release as much of the coated drug in a time frame as short as possible to shorten the inflation time to an absolute minimum. Thus it was surprising and unexpected that a catheter balloon coated with Paclitaxel and shellac resulted in a profound increase of drug release compared to a catheter balloon that was not coated with shellac. WO 2008/046641 rather implied that shellac combined with a drug leads to a stable formulation that releases the drug very slowly over a long time period (months) and would not be suitable for fast drug release. Catheter balloons coated with the method according to the invention resulted in an up to 20-fold higher tissue concentration as compared with prior art balloon types (Posa et al., Coron Artery Dis, 2008, 19, 243-7), reaching an optimal tissue concentration for inhibition of smooth muscle cell proliferation already after dilation for 30 s. The efficacy of short Paclitaxel exposure onto the vessel wall was shown by significant smaller neointimal hyperplasia in the overstretch injury model as compared with the uncoated catheter balloon (FIG. 4). If applicable the inflation time can be shortened even further to control the amount of drug that is released into the tissue. Alternatively, the amount of drug coating on the catheter balloon can be reduced, since the release of the drug is much more efficient, up to 20-times, in comparison to known coated catheter balloons. Consequently it was not obvious to a skilled person that shellac would increase efficacy of a Paclitaxel coated catheter balloon and would allow further reduction of the dilatation time. Rather in contrast a skilled person would expect on the basis of the results disclosed for the Paclitaxel-shellac-coated stent that the presence of shellac would prolong the release of Paclitaxel which would lead to longer dilatation times in order to achieve sufficient Paclitaxel tissue concentrations.

Using the catheter balloon coated with Paclitaxel and shellac horizontal/longitudinal (adjacent reference segments) distribution of Paclitaxel as well as vertical drug penetration into the tissue up to deepness of 2 mm was achieved; this allows effective drug concentrations even in the presence of a thick plaque of an atherosclerotic coronary artery. The use of a catheter balloon coated with Paclitaxel and shellac resulted in an up to 20-fold higher tissue concentration as compared with balloon types coated only with Paclitaxel, reaching an optimal tissue concentration for inhibition of smooth muscle cell proliferation. The balloon inflation time-dependency study showed maximum tissue Paclitaxel concentration after balloon inflation times of 30 s, with minimal further increase in tissue drug concentration after 45 s, and release of the drug into the circulation after a 1-min inflation time. The balloon inflation time of 30 s causes less arterial injury and is better tolerated by patients in a clinical scenario. A study also demonstrates the efficacy of short Paclitaxel exposure onto the vessel wall as shown by significant smaller neointimal hyperplasia in the overstretch injury model as compared with the conventional balloon. The studies were conducted with catheter balloons coated with Paclitaxel and shellac, wherein the weight ratio was from 100:1 to 1:100. The Paclitaxel release was best at ratios from 10:1 to 1:10, however Paclitaxel release could be measured from up to 100:1 to 1:100 Paclitaxel and shellac ratio.

Compared to drug eluting stents, in which about 85% of the stented plaque surface is not covered by struts, catheter balloon coated with Paclitaxel and shellac allow a homogenous distribution of an antiproliferative compound, which goes beyond the area directly covered by the stent struts. In addition, this uniformity of deliverance enhances the efficacy of the drug to the vessel wall. The drug concentration within the vessel wall is highest at the time of injury when the inflammatory and proliferative processes are most vigorous. Comparing fluorescent Paclitaxel-conjugate coated balloons and stents with polymer carrier coating, we could demonstrate that only a small amount of Paclitaxel was distributed unevenly on the vessel wall after use of a drug eluting stent; in contrast we found a uniform distribution of high amounts of Paclitaxel when the catheter balloon coated according to the invention was used. Using the overstretch injury model of the coronary arteries, the catheter balloon coated with Paclitaxel and shellac results in less neointimal hyperplasia as compared with conventional balloon use, even without complementary stent implantation. The injury score was relatively low, with complete endothelialization in both groups, in spite of the 1.3:1 balloon:artery ratio, indicating a rapid healing process after balloon overstretch injury. Furthermore, the fibrin and inflammation scores were also relatively low, and no foreign body reaction or granulomatous reaction was found. These findings highlight the advantages of the exclusive use of the catheter balloon coated with Paclitaxel and shellac especially when compared to the histopathological consequences of coronary stent implantations.

In one embodiment the catheter balloon coated with Paclitaxel and shellac is further characterized in that after balloon inflation for 30 s preferably >26% of Paclitaxel are released from the balloon surface, more preferably >30%, more preferable >40%, further more preferable >50%, even more preferable >60% and most preferable >70%. Consequently, a dilatation time for a single dilatation of ≤30 seconds is preferred. Moreover a total dilatation time of ≤60 seconds is preferred which means that the single dilatation of ≤30 seconds is repeated once.

In another embodiment the catheter balloon coated with Paclitaxel and shellac is further characterized in that after balloon inflation for 30 s Paclitaxel tissue concentration of preferably >10 µM/L, more preferable >30 µM/L, even more preferable >50 µM/L, further more preferable >80 µM/L, even more preferable >100 µM/L, further preferable 120 µM/L, most preferable >140 µM/L can be achieved in the dilated segment 45 min post-dilatation.

In a further preferred embodiment catheter balloon coated with Paclitaxel and shellac is further characterized in that after balloon inflation for 15 s Paclitaxel tissue concentrations of preferably >1 µM/L, more preferable >3 µM/L, even more preferable >5 µM/L, further more preferable >8 µM/L, even more preferable >10 µM/L, further preferable 15 µM/L, most preferable >20 µM/L can be achieved in the dilated segment 45 min post-dilatation.

In another embodiment the catheter balloon is coated with Paclitaxel and shellac, wherein the weight ratio of Paclitaxel to shellac is from 100:1 to 1:100, preferably 95:1 to 1:95, more preferable 90:1 to 1:90, more preferable 85:1 to 1:85, further preferable 80:1 to 1:80, more preferable 75:1 to 1:75, more preferably 70:1 to 1:70, more preferable 65:1 to 1:65, more preferable 60:1 to 1:60, more preferable 55:1 to 1:55, more preferable 50:1 to 1:50, more preferable 45:1 to 1:45, more preferable 40:1 to 1:40, more preferable 35:1 to 1:35, more preferable 30:1 to 1:30, more preferable 25:1 to 1:25, more preferable 20:1 to 1:20, even more preferable 15:1 to 1:15, further preferable 10:1 to 1:10 and most preferable 5:1 to 1:5.

The paclitaxel concentration in the fresh frozen artery walls and balloon surface was measured by high-performance liquid chromatography (HPLC). After thawing, the tissues were weighed at ambient temperature and, depending on weight different volumes of ethanol were added to the samples (sufficient ethanol to cover the tissue completely). The samples were then treated with ultrasound for 40 min, and 200-µL aliquots were then centrifuged and stored for subsequent measurements. A calibration line was produced in the range between 50 and 5000 ng/mL. For the measurement of the remaining Paclitaxel concentration on the balloon surface, the catheter balloon was immersed in Ethanol (>96%) for 5 minutes. The obtained solution was vortexed for another 5 minutes and then centrifuged. The supernatant was used for measurement via HPLC. The samples for the calibration line were prepared by dilution of a stock solution with a concentration of 1000 µg/mL. Aliquots of all samples (samples from tissue or balloon and calibration line) were transferred into auto-sampler vials and the same volume of 0.1% formic acid was added. The flow rate of the HPLC system was 0.2 mL/min through a column of ODS Hypersil (ThermoElectron Corporation), particle size 5µ, pore size 120 Å. The isocratic mobile phase consisted of 70% methanol and 30% 0.1% formic acid. Paclitaxel was detected by mass spectrometry in multiple reaction monitoring mode with a transition of paclitaxel from 854 to 105 AMU. The tissue paclitaxel concentration was expressed in µM/L, which measure is independent from the sample weight.

Any commercially available dilatable catheter balloon may be used as catheter balloon. Preferably, so called multifold balloons are used, as described for example in the international patent application WO 94/23787 A1 by David H. Rammler, Labintelligence, USA; or the international patent application WO 03/059430 A1 by Scimed Life Sciences, Inc., USA; or the international patent application WO 2004/028582 A1 by Prof. Dr. Ulrich Speck or the European Patent No. EP 0519063 B1 by Medtronic Inc., USA.

Such balloons are provided with folds or wings forming essentially closed cavities when the balloon is in its compressed state but bending outward during dilatation and being capable of releasing substances contained in the folds or respectively of pressing said substances against the vessel wall.

Such balloons are advantageous since the substances enclosed in the folds or respectively paclitaxel enclosed in the folds are protected from being detached too soon during the insertion of the catheter.

To protect the active agent paclitaxel from early detachment from the catheter balloon, paclitaxel may also be incorporated or embedded into a carrier substance, preferably a polymeric carrier. A most preferred biological biodegradable polymeric carrier is shellac. Regardless the source of shellac, all kinds of shellac types obtained from various locations or from different insects were able to achieve the inventive results so that any kind or sort of shellac can be used in the present invention. Thus there are no limitations in regards of shellac.

Shellac is a natural resin produced from the glandular secretion of a number of species of lac-producing insects. Lac insects belong to the order of Hemiptera, superfamily Coccoidea such as Metatachardia, *Laccifer*, Tachordiella, and others, however, members of two families—Lacciferidae and Tachardinidae are more prominent in lac secretion. The one that is commercially cultured is *Kerria lacca*, which is also known by such synonyms as *Laccifer lacca* Ker, *Tachardia lacca*, and *Carteria lacca*. *Kerria lacca* is an Indian scale insect, which infests branches of numerous trees from the East Indies, such as *Butea frondos* Rosch, *Acacia arabica* Willd and *Ficus religiosa* Linn. Shellac is the only commercially used natural resin of animal origin and is quite different from all other natural resins. More recently, as a new awareness about the environments and the toxicity of chemical raw-material is noticeable everywhere, shellac or shellac modified resin are gaining importance due to their interesting and unique characteristics. Broken branches are sold as stick lac and, after grounding and washing with water to eliminate wood and red pigments (lac dye), seed lac is obtained. Purification of seed lac gives the more homogeneous product known as shellac. Its use in Europe began towards the end of the 16$^{th}$ century mainly as a varnish (mostly known as "French polish") for wooden objects, musical instruments and gilding, as a protective for vinyl disks and mural paintings, as an insulating material for earlier radios and other electrical tools and as an adhesive in the restoration of pottery.

Raw material shellac consists of 70-80% resin, 4-8% dye, 6-7% hard and high gloss finished wax, 3% water, up to 9% vegetable and animal impurities and aroma substances. Shellac resin is a complicated mixture of aliphatic (60%) and sesquiterpenoid acids (32%) and their esters. Sesquiterpenoid acids are jalaric and laccijalaric acids (structure I and II) and aliphatic acids are aleuritic (Ill) and butolic acid.

A possibility for chemical description of resin molecule is a structure model where in each case 4 molecules jalaric or laccijalaric acid and aleuritic acid are connected by ester bonding alternately.

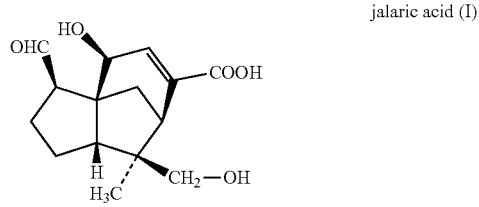

jalaric acid (I)

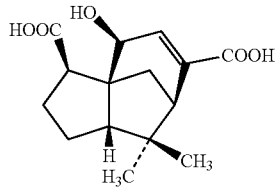

laccijalaric acid (II)

Its chemical composition is almost constant, although the amount of some components changes depending on the nature of host trees on which the insects grows. By Cannizzaro-type disproportionation under alkaline hydrolysis will be synthesized from these acids shellolic acid (IV) and deviate compounds. Purified shellac consists of two main components. These components are 9,10,16-trihydroxypalmitic acid (aleuritic acid) CAS [53-387-9] and shellolic acid (IV).

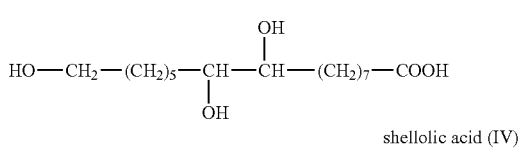

aleuritic acid (III)

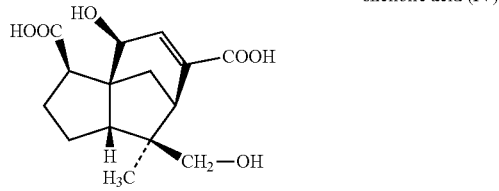

shellolic acid (IV)

A modification with other natural or synthetic resins or co-polymerization with various monomers is possible to cross link shellac, modified shellac resins and shellac copolymers with urea, melamine, formaldehyde, isocyanides, other chemical processes like polymerization, hydroxylation, extrication, etc. are possible.

Followings are the commercial grades of shellac:
Seedlac
Hand Made Shellac
Machine Made Shellac
Dewaxed Shellac
Dewaxed Bleached Shellac
Aleuritic Acid
Major Properties of shellac are:
Shellac is a hard natural resin
Shellac has a good resistance against solvent
Shellac based on hydrocarbons
Shellac is non toxic
Shellac is thermoplastic
Shellac is physiologically harmless
Shellac is approved for various applications in the food industry.
Shellac is not UV-resistant
Shellac is soluble in lower alcohol's
Shellac has excellent dielectric properties high dielectric strength, low dielectric constant, good tracking resistance etc.
Shellac has a low melting point (65-85° C.).
Shellac is water soluble in water-alkaline solutions Coatings do not change their electric properties under UV-radiation.

Shellac has excellent film forming properties.

Shellac has low thermal conductivity and a low coefficient of expansion forms smooth, high gloss films and surfaces.

Shellac coating has excellent adhesion to many coatings and can be polished.

Shellac can be cross linked to modify other natural/synthetic resins Examples for industrial uses:

Coating of pills & tablets
Coating Fruits
Cosmetics
French polish surface coating, sealer
Optical frames The catheter balloons according to the invention were coated with different commercial grades of shellac as well as with varying batches, which differed in the Lac insects, and host tree types used as well as in the time of harvest. There were no differences in Paclitaxel release observable in the various Paclitaxel-shellac coated catheter balloons.

In order to apply said carrier shellac or other additional carrier onto the catheter balloon surface, the carrier substance can be added to the solution of paclitaxel or can be applied as second solution without or even again with paclitaxel. Such solutions containing paclitaxel and/or shellac and optionally further carrier substances are then applied onto the catheter balloon surface using conventional coating methods, in particular spattering, spraying or dipping methods. Suitable additional carriers are such substances which are also used as balloon material, in particular polymeric and polymerizable substances as listed further below.

Also in such cases where the coating, i.e. the paclitaxel, is not protected by the folds of a multifold balloon or where the paclitaxel is not incorporated into a larger excess of shellac, a sufficient amount of the pure active agent paclitaxel may be applied onto the catheter balloon so that even including a calculated amount of The paclitaxel is embedded into the shellac, preferably in the range of about 30% of the total amount being detached prematurely during the insertion of the catheter balloon, so that there is still a sufficiently high and therapeutically active amount of paclitaxel present on the balloon once it has reached its target position.

Thus, it is preferred to protect the active agent paclitaxel from premature detachment by embedment into the shellac on the surface of the catheter balloon and optionally underneath the folds of the balloon.

Generally, an amount of 0.1 μg to 30 μg of paclitaxel per mm$^2$ of the surface of the balloon catheter to be coated can be applied onto the surface of the balloon catheter, while an amount of 0.5 μg/mm$^2$ to 6 μg/mm$^2$ of paclitaxel are sufficient in order to achieve the desired effect on restenosis prophylaxis. Preferably the amount of paclitaxel per mm$^2$ balloon surface is between 1 μg/mm$^2$ and 5 μg/mm$^2$, more preferably between 1.5 μg/mm$^2$ and 4.5 μg/mm$^2$, still more preferably between 2.0 μg/mm$^2$ and 4.0 μg/mm$^2$, and most preferably between 2.5 μg/mm$^2$ and 3.5 μg/mm$^2$.

Preferred is also a total amount of 10 to 1000 μg of paclitaxel per catheter balloon and most preferably 20μ to 400 μg per catheter balloon.

Paclitaxel is commercially available from several suppliers. Paclitaxel is known under the trademark name of Taxol® and is also designated with various synonymous names such as:

BMS 181339-01, BMS-181339, BMS-181339-01, Capxol, DRG-0190, DTS-301, Ebetaxel, Genaxol, Genexol, Genexol-PM, HSDB 6839, Intaxel, KBio2_002509, KBio2_005077, KBio2_007645, KBio3_002987, KBioGR_002509, KBioSS_002517, LipoPac, MBT 0206, MPI-5018, Nanotaxel, NCI60_000601, Nova-12005, NSC 125973, NSC-125973, NSC125973, Onxol, Pacligel, Paxceed, Paxene, Paxoral, Plaxicel, QW 8184, SDP-013, TA1, Tax-11-en-9-on, TaxAlbin, Taxol A, Xorane or Yewtaxan.

Its chemical structure is as follows:

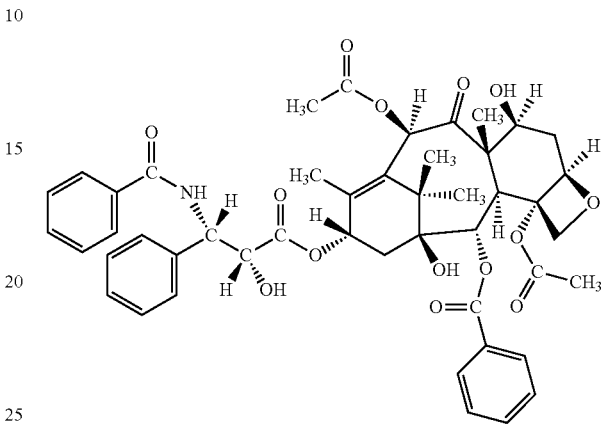

IUPAC nomenclature is as follows: [2aR-[2a,4,4a,6,9(R*, S*),11,12,12a,12b]]-(benzoylamino)-hydroxybenzene propionic acid 6,12b-bis-(acetyloxy)-12-(benzoyloxy)-2a-3, 4, 4a, 5, 6, 9, 10, 11, 12, 12a, 12b-dodecahydro-4,11-dihydroxy-4a,8,13,13-tetramethyl-5-oxo-7,11-methano-1H-cyclodeca[3,4]benz[1,2-b]oxet-9-yl ester).

Paclitaxel is highly soluble in dimethyl sulfoxide (DMSO) and methanol as well as in anhydrous ethanol, but is comparatively poorly soluble in water. Paclitaxel is especially stable at a pH between 3 and 5 and can be stored for long periods, whereas it is comparatively instable at alkaline pH.

Dimethyl sulfoxide (DMSO), acetone, ethyl acetate, ethanol and methanol are used as a solvent for paclitaxel. Materials used for the balloon catheter are such materials as listed further below, wherein the following polymers are particularly preferred: polyamides, block copolymers of polyamide, polyether and polyester, polyurethanes, polyesters and polyolefins.

The inventive coating procedure can be performed in two alternatives ways. A catheter balloon and preferably a uncoated catheter balloon or a catheter balloon without any releasable active agent in its surface is provided. Than a solution of paclitaxel together with shellac in a suitable solvent such as acetone, ethyl acetate, ethanol, methanol, DMSO, THF, chloroform, methylene chloride or the like is prepared and applied using conventional coating methods such as spray coating, dip coating etc. in order to obtain after the drying step a solid paclitaxel-shellac coating on the surface of the catheter balloon (steps I+IIA+IIA+IV).

An alternative way is to prepare a paclitaxel solution and a second shellac solution and to apply both solutions simultaneously or subsequently in order to obtain after the drying step a solid paclitaxel-shellac coating on the surface of the catheter balloon (steps I+IIB+IIIB+IV).

The coating steps IIA) and IV) or IIIB) and IV) respectively can be repeated several times in the inventive coating methods. Usually, the coating procedure is repeated one or two or three times, but said repetition is not obligatory. Even one coating procedure may be sufficient for the application of the required amount of paclitaxel and shellac onto the catheter balloon.

The drying step IV) can be performed at room temperature or at elevated temperatures to up to 50° C. and at atmospheric pressure or under reduced pressure to high vacuum. If the coating steps III) [IIA) or IIIB)] is repeated, the drying steps IV) are conducted at room temperature and atmospheric pressure, while preferably after the last coating step of the circle the drying step is more intensive, i.e. longer or with vacuum or with elevated temperature.

The catheter balloon is dilatable or expandable and is most preferably an angioplasty catheter balloon which could be used without crimped stent or with a crimped stent. As stent, all kinds of common stents, such as self-expandable stents, not self-expandable stents, metal stents, polymer stents, biodegradable stents, bifurcation stents, uncoated (bare) stents, polymer coated stents, drug release coated stents, stents with a pure active agent coating etc. can be used.

Moreover, the stent can be crimped on the catheter balloon before the inventive coating procedure is carried out so that catheter balloon and stent are coated together with a shellac-paclitaxel coating. If the catheter balloon is coated first and the stent is crimped on the balloon thereafter, a paclitaxel coated stent or a paclitaxel-shellac coated stent could be used having the same or different concentration of paclitaxel and/or shellac on the surface.

However, it is preferred to use the coated catheter balloon of the present invention without stent.

The provided catheter balloon is normally a multifold catheter balloon which will also coated under or within the folds. Moreover it is possible to selectively coat or fill the folds. The coating within or under the folds has the advantage that during insertion of the catheter balloon the coating and thus the paclitaxel is protected against being washed off by the blood stream.

Furthermore, the catheter balloon can be coated in its expanded (inflated) or deflated state.

The preferred solvents for shellac and paclitaxel are volatile easily removable solvents such as acetone, ethyl acetate, ethanol, methanol, DMSO (dimethyl sulfoxide), THF (tetrahydrofurane), chloroform, methylene chloride.

The total surface load with paclitaxel and shellac of the catheter balloon is between 1 µg/mm$^2$ and 12 µg/mm$^2$. Preferably the amount of paclitaxel and shellac present on the coated balloon surface is between 2 µg/mm$^2$ and 10 µg/mm$^2$ balloon surface, more preferably between 3 µg/mm$^2$ and 9 µg/mm$^2$, still more preferably between 4 µg/mm$^2$ and 8 µg/mm$^2$, still more preferably between 5 µg/mm$^2$ and 7 µg/mm$^2$, and most preferably between 5.5 µg/mm$^2$ and 6.5 paclitaxel and shellac per mm$^2$ balloon surface (µg/mm$^2$).

The inventive coating method can optionally further comprise the step V):

V) Sterilization of the paclitaxel and shellac coated catheter balloons.

The sterilization is most preferably performed with ethylene oxide.

Moreover, the inventive coating method can optionally further comprise the step IB):

IB) Protecting the parts of the balloon catheter which should not be coated with a removable protection sheet.

Since the catheter balloon is only one part of the balloon catheter, the surfaces of the balloon catheter with should not be coated with the paclitaxel-shellac composite can be protected by a removable protection sheet such as a plastic bag or plastic foil and only the catheter balloon is left free so that only the free part will be coated. After the coating process is completed, the protection sheet is removed.

The inventive balloon coating method can optionally also further comprise the step VI):

VI) Protecting the coated catheter balloon with a removable protection cover.

The removable protection cover is useful to protect the catheter balloon and especially the coating on the catheter balloon.

As described below in detail, the surface of the catheter balloon is textured, smooth, rough, harsh, provided with cavities or provided with channels open towards the outside of the balloon.

The coating solution containing paclitaxel can optionally contain at least one further carrier substance. Said at least one further carrier substance is selected from the group consisting of:

parylene C, parylene D, parylene N, parylene F, polyvalerolactones, poly-ε-decalactone, polylactonic acid, polyglycolic acid, polylactides, polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerate, poly(1,4-dioxane-2,3-dione), poly(1,3-dioxane-2-one), poly-paradioxanone, polyanhydrides, polymaleic acid anhydride, polyhydroxymethacrylates, fibrin, polycyanoacrylate, polycaprolactone dimethylacrylates, poly-ß-maleic acid, polycaprolactone butyl acrylates, multiblock polymers from oligocaprolactonedioles and oligodioxanonedioles, polyether ester multiblock polymers from PEG and poly(butylene terephthalate), polypivotolactones, polyglycolic acid trimethyl carbonates, polycaprolactone glycolides, poly(γ-ethyl glutamate), poly(DTH-iminocarbonate), poly(DTE-co-DT-carbonate), poly(bisphenol A-iminocarbonate), polyorthoesters, polyglycolic acid trimethyl-carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide soft polyurethanes, polyurethanes having amino acid residues in the backbone, polyether esters, polyethylene oxide, polyalkene oxalates, polyorthoesters as well as their copolymers, lipids, carrageenans, fibrinogen, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and derivatives thereof, heparan sulfates and derivatives thereof, heparins, chondroitin sulfate, dextran, ß-cyclodextrins, copolymers with PEG and polypropylene glycol, gum arabic, guar, gelatin, collagen N-hydroxysuccinimide, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylene, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM gums, fluorosilicones, carboxymethyl chitosans, polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, silicones, polysiloxanes, polydimethylsiloxanes, polyvinyl halogens and copolymers, cellulose ethers, cellulose triacetates, chitosans and copolymers and/or mixtures of the aforementioned polymers.

In the case, a textured surface of the catheter balloon is desired, the surface of the catheter balloon can be textured mechanically, chemically, electronically and/or by means of radiation to allow for an improved adhesion of paclitaxel and to assist the precipitation or crystallization of the paclitaxel.

By the texturing of the surface of the catheter balloon the surface of the catheter balloon is to be modified in the range from nanometers to micrometers, i.e. a kind of micro-rough surface structure is to be provided. Surface texturing is preferably applied to the whole area to be coated of the catheter balloon and may result in organized or random structures.

The catheter balloons may be composed of the following materials:

parylene C, parylene D, parylene N, parylene F, polyvalerolactones, poly-ε-decalactone, polylactonic acid, polyglycolic acid, polylactides, polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerate, poly(1,4-dioxane-2-dione), poly(1,3-dioxane-2-one), poly-paradioxanone, polyanhydrides, polymaleic acid anhydride, polyhydroxymethacrylates, fibrin, polycyanoacrylate, polycaprolactone dimethylacrylates, poly-ß-maleic acid, polycaprolactone butyl acrylates, multiblock polymers from oligocaprolactonedioles and oligodioxanonedioles, polyether ester multiblock polymers from PEG and poly(butylene terephthalate), polypivotolactones, polyglycolic acid trimethyl carbonates, polycaprolactone glycolides, poly(γ-ethyl glutamate) poly(DTH-iminocarbonate), poly(DTE-co-DT-carbonate), poly(bisphenol A-iminocarbonate), polyorthoesters, polyglycolic acid trimethyl-carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide, soft polyurethanes, polyurethanes having amino acid residues in the backbone, polyether ester, polyethylene oxide, polyalkene oxalates, polyorthoesters as well as their copolymers, lipids, carrageenans, fibrinogen, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and derivatives thereof, heparan sulfates and derivatives thereof, heparins, chondroitin sulfate, dextran, ß-cyclodextrins, copolymers with PEG and polypropylene glycol, gum arabic, guar, gelatine, collagen N-hydroxysuccinimide, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM gums, fluorosilicones, carboxymethyl chitosans, polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, silicones, polysiloxanes, polydimethylsiloxanes, polyvinyl halogens and copolymers, cellulose ethers, cellulose triacetates, chitosans and copolymers and/or mixtures of the aforementioned polymers.

Polyamides, block copolymers of polyamide-polyetherpolyester, polyurethanes, polyester and polyolefins are preferred.

It is of importance to avoid all damage to the catheter balloons while the balloon surface is textured and to ensure that their capability to expand is not disadvantageously affected. Thus, the methods for micro texturing the balloon surface must not lead to the formation of holes, micropores or fissures in the balloon material. Ideally, only the outer surface of the balloon, i.e. to a maximum depth of 1 μm, is textured.

The dilatable catheter balloon may be textured mechanically by making use of a rasp-like device, a rasp or a blasting method employing solid particles, such as a sand blasting procedure.

In a chemical-mechanical procedure a suspension or a dispersion of solid particles in a solvent, in particular in water, is used. Such methods are also referred to as chemical polishing methods. By rubbing such compositions onto the surface of the balloon material the material is roughened without deep fissures or holes being created.

In a purely chemical texturing method, acids, bases, etching chemicals and/or oxidizing chemicals corroding the surface of the balloon material are used. Such chemicals, however, are to be used with caution, as the balloon material could be damaged if the exposition period is to long or too intense.

When an electrical or electronic procedure is used for texturing the surface of the dilatable catheter balloon, texturing is performed by means of conductors which are heated by current flow. For example, a fine, warm, hot or glowing needle may be used to melt the surface of the balloon material by means of which certain patterns can be created on the surface, especially when the needle is moved along the surface of the catheter balloon.

An elegant method for generating organized textures, especially in form of micro depressions or micro channels, can consist in the use of lasers or basically of strongly focused radiation. Said radiation means are very accurate and may be especially used for the generation of defined textures such as grids, spirals or lines.

The textured or micro modified to nano-modified surface of the catheter balloon as well as the not textured catheter balloons may be wetted before applying the coating solution by using all common methods in order to increase adhesion of the coating to the balloon surface.

Any kind of common coating process can be used to apply the paclitaxel-shellac solution or the paclitaxel solution and the shellac solution onto the balloon surface such as spray coating, brush coating, dip coating, vapour deposition, pipetting and the like.

The content of paclitaxel in the paclitaxel containing solution is between 1 μg to 1 mg paclitaxel per ml solution, preferably between 10 μg to 500 μg of paclitaxel per 1 ml solution, more preferably between 30 μg to 300 μg of paclitaxel per 1 ml solution, and most preferably between 50 μg to 100 μg of paclitaxel per 1 ml solution. For example, the solution of paclitaxel in ethanol, acetone, ethyl acetate or DMSO may be applied onto the balloon surface by means of spattering, dipping, plasma deposition, brushing or spraying. While the whole surface of the catheter balloon is usually coated when a dipping method or plasma disposition are used, spattering, brushing and spraying may be used when only a portion of the balloon surface is to be coated.

According to the invention, the catheter balloon does not have to be completely coated. Partial coating of the catheter balloon or partial loading of certain texture elements onto the surface of the catheter balloon may be sufficient. A special catheter balloon including micro-needles or micro-pores or micro-chambers is disclosed in the international patent application no. WO 02/043796 A2 issued to Scimed Life Systems, Inc., USA, wherein inflatable and textured areas are present on the balloon surface. In said embodiment, loading or inflating certain portions of the balloon surface would be sufficient to achieve the desired therapeutic success, wherein it is also possible, evidently, that the whole surface is coated.

An example where it is desirable to coat the catheter balloon only partially is the valvuloplasty. Balloon valvuloplasty is a procedure in which a narrowed heart valve is stretched open using a procedure that does not require open heart surgery. In some people the valves are too narrow. Balloon valvuloplasty is performed to improve valve function and blood flow by enlarging the valve opening. It is a treatment for aortic, mitral, and pulmonary stenosis. In balloon valvuloplasty, a thin catheter balloon is inserted through the skin in the groin area into a blood vessel, and then is threaded up to the opening of the narrowed heart valve. The balloon is inflated to stretch the valve open and relieve the valve obstruction. The prevention of restenosis is also of concern, however, catheter balloons that are coated at the whole surface are not suitable, because only a small part in the middle of the catheter balloon is in contact with the valve, wherein the rest of the catheter balloon lies in the ventricle and the atria of the heart. After inflation of the balloon, the walls in the ventricle and atria of the heart come also in contact with the fully drug coated catheter balloon, which is not desirable and could lead to severe side effects. The catheter balloon according to the invention is only coated at the area that comes in direct contact with the valve and where an inhibition of restenosis is wanted. Thus a preferred embodiment of the present invention is a catheter balloon coated with shellac and paclitaxel only around that part of the catheter balloon which comes into contact with the heart valve. Another preferred embodiment of the present invention is directed to a catheter balloon which is completely coated with shellac but which is coated with paclitaxel only around that part of the catheter balloon which comes into contact with the heart valve.

Furthermore, another possibility consists in coating the catheter balloon partially, i.e. certain sections of the catheter balloon and, successively, additional areas until a completely coated catheter balloon is obtained, if desired.

It has been found that complete or partial wetting of the surface of the catheter balloon which should be coated has an advantageous effect in that regard that the adhesion of the paclitaxel-shellac coating to the balloon surface is increased if certain solvents or concentrations are used for the paclitaxel and/or shellac containing solution.

Since the paclitaxel-shellac coating is hard to characterize, the present invention relates also to paclitaxel-shellac coated catheter balloons obtained according to the inventive coating method disclosed herein as well as to balloon catheter and dilatation catheter comprising said paclitaxel-shellac coated catheter balloon.

Furthermore, another active agent may be added to the paclitaxel containing solution. Said further active agent can be selected from the following group comprising or consisting of:

abciximab, acemetacin, acetylvismione B, aclarubicin, ademetionine, adriamycin, aescin, afromosone, akagerine, aldesleukin, amidorone, aminoglutethimide, amsacrine, anakinra, anastrozole, anemonin, anopterine, antimycotics, antithrombotics, apocymarin, argatroban, aristolactam-AII, aristolochic acid, ascomycin, asparaginase, aspirin, atorvastatin, auranofin, azathioprine, azithromycin, baccatin, bafilomycin, basiliximab, bendamustine, benzocaine, berberine, betulin, betulinic acid, bilobol, bisparthenolidine, bleomycin, combrestatin, Boswellic acids and derivatives thereof, bruceanol A, B and C, bryophyllin A, busulfan, antithrombin, bivalirudin, cadherins, camptothecin, capecitabine, o-carbamoyl-phenoxyacetic acid, carboplatin, carmustine, celecoxib, cepharanthin, cerivastatin, CETP inhibitors, chlorambucil, chloroquine phosphate, cicutoxin, ciprofloxacin, cisplatin, cladribine, clarithromycin, colchicine, concanamycin, coumadin, C-type natriuretic peptide (CNP), cudraisoflavone A, curcumin, cyclophosphamide, ciclosporin A, cytarabine, dacarbazine, daclizumab, dactinomycin, dapsone, daunorubicin, diclofenac, 1,11-dimethoxycanthin-6-one, docetaxel, doxorubicin, daunamycin, epirubicin, epothilone A and B, erythromycin, estramustine, etoposide, everolimus, filgrastim, fluroblastin, fluvastatin, fludarabine, fludarabine-5'-dihydrogen phosphate, fluorouracil, folimycin, fosfestrol, gemcitabine, ghalakinoside, ginkgol, ginkgolic acid, glycoside 1a, 4-hydroxyoxycyclo phosphamide idarubicin, ifosfamide, josamycin, lapachol, lomustine, lovastatin, melphalan, midecamycin, mitoxantrone, nimustine, pitavastatin, pravastatin, procarbazine, mitomycin, methotrexate, mercaptopurine, thioguanine, oxaliplatin, irinotecan, topotecan, hydroxycarbamide, miltefosine, pentostatin, pegaspargase, exemestane, letrozole, formestane, mitoxantrone, mycophenolate mofetil, ß-lapachone, podophyllotoxin, podophyllic acid 2-ethylhydrazide, molgramostim (rhuGM-CSF), peginterferon α-2b, lenograstim (r-HuG-CSF), macrogol, selectin (cytokine antagonist), cytokinin inhibitors, COX-2 inhibitor, angiopeptin, monoclonal antibodies inhibiting muscle cell proliferation, bFGF antagonists, probucol, prostaglandins, 1-hydroxy-11-methoxycanthin-6-one, scopoletin, NO donors, pentaerythrityl tetranitrate and sydnoimines, S-nitroso derivatives, tamoxifen, staurosporine, β-estradiol, α-estradiol, estriol, estrone, ethinyl estradiol, medroxyprogesterone, estradiol cypionates, estradiol benzoates, tranilast, kamebakaurin and other terpenoids used in cancer therapy, verapamil, tyrosine kinase inhibitors (tyrphostins), paclitaxel and derivatives thereof, 6-α-hydroxy-paclitaxel, taxoteres, mofebutazone, lonazolac, lidocaine, ketoprofen, mefenamic acid, piroxicam, meloxicam, penicillamine, hydroxychloroquine, sodium aurothiomalate, oxaceprol, β-sitosterol, myrtecaine, polidocanol, nonivamide, levomenthol, ellipticine, D-24851 (Calbiochem), colcemid, cytochalasin A-E, indanocine, nocodazole, bacitracin, vitronectin receptor antagonists, azelastine, guanidyl cyclase stimulator, tissue inhibitor of metal proteinase-1 and -2, free nucleic acids, nucleic acids incorporated into virus transmitters, DNA and RNA fragments, plasminogen activator inhibitor 1, plasminogen activator inhibitor 2, antisense oligonucleotides, VEGF inhibitors, IGF-1, active agents from the group of antibiotics, cefadroxil, cefazolin, cefaclor, cefoxitin, tobramycin, gentamicin, penicillins, dicloxacillin, oxacillin, sulfonamides, metronidazole, enoxaparin, heparin, hirudin, PPACK, protamine, prourokinase, streptokinase, warfarin, urokinase, vasodilators, dipyramidole, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, ß und γ, histamine antagonists, serotonin blockers, apoptosis inhibitors, apoptosis regulators, halofuginone, nifedipine, tocopherol, tranilast, molsidomine, tea polyphenols, epicatechin gallate, epigallocatechin gallate, leflunomide, etanercept, sulfasalazine, dicloxacillin, tetracycline, triamcinolone, mutamycin, procainimide, retinoic acid, quinidine, disopyramide, flecainide, propafenone, sotalol, natural and synthetically obtained steroids such as bryophyllin A, inotodiol, maquiroside A, ghalakinoside, mansonine, strebloside, hydrocortisone, betamethasone, dexamethasone, nonsteroidal substances (NSAIDS) such as fenoprofen, fenoprofen, ibuprofen, indomethacin, naproxen, phenylbutazone, antiviral agents, acyclovir, ganciclovir zidovudine, clotrimazole, flucytosine, griseofulvin, ketoconazole, miconazole, nystatin, terbinafine, antiprotozoal agents, chloroquine, mefloquine, quinine, natural terpenoids, hippocaesculin, barringtogenol-C21-angelate, 14-dehydroagrostistachin, agroskerin, agrostistachin, 17-hydroxyagrostistachin, ovatodiolids, 4,7-oxycycloanisomelic acid baccharinoids B1, B2, B3 and B7, tubeimoside, bruceantinoside C, yadanziosides N and P, isodeoxyelephantopin, tomenphantopin A and B, coronarin A, B C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-α-senecioyloxychaparrin, taxamairin A and B, regenilol, triptolide, cymarin, hydroxyanopterine, protoanemonin, cheliburin chloride, sinococuline A and B, dihydronitidine, nitidine chloride, 12-β-hydroxypregnadien-3, 20-dione, helenalin, indicine, indicine-N-oxide, lasiocarpine, inotodiol, podophyllotoxin, justicidin A and B, larreatin, malloterin, mallotochromanol, isobutyrylmallotochromanol, marchantin A, maytansin, lycoridicin, margetine, pancratistatin, liriodenine, oxoushinsunine, periplocoside A, deoxypsorospermin, psychorubin, ricin A, sanguinarine, manwu wheat acid, methylsorbifolin, chromones of spathelia, stizophyllin, dihydrousambaraensine, hydroxyusambarine, strychnopentamine, strychnophylline, usambarine, usambarensine, liriodenine, daphnoretin, lariciresinol, methoxylariciresinol, syringaresinol, sirolimus (rapamycin), somatostatin, tacrolimus, roxithromycin, troleandomycin, simvastatin, rosuvastatin, vinblastine, vincristine, vindesine, teniposide, vinorelbine, trofosfamide, treosulfan, temozolomide, thiotepa, tretinoin, spiramycin, umbelliferone, desacetylvismione A, vismione A and B, zeorin.

Furthermore, the present invention relates to dilatable and expandable catheter balloons and in particular to multifold balloons for catheters coated according to an inventive method.

The catheter balloons are coated with essentially pure paclitaxel. Thus, the catheter balloons carry a layer consisting of active agent in form of paclitaxel incorporated into the biopolymer shellac, wherein in said layer only traces of solvents are present, while optionally another active agent and/or another carrier substance may be present in a same or different amount as the paclitaxel or the shellac.

Due to the inventive coating method, the paclitaxel-shellac composite dried at the surface of the catheter balloon has a special consistence, which is hard to characterize but seems to be essential for the transfer to the cell wall and the incorporation, especially into the smooth muscle cells.

In the case of multifold balloons, one part of the paclitaxel-shellac containing coating is provided underneath the folds when the balloon is in its compressed, i.e. deflated state. Said amount is sufficient to achieve the desired therapeutic success even if the remaining uncovered balloon surface is not coated with the active agent paclitaxel.

Thus, the present invention also relates to balloon catheters comprising a catheter balloon coated according to the present invention with paclitaxel and shellac and optionally a further active agent and/or optionally a further carrier substance or matrix substance.

Such catheters are preferably used for treating constricted vessel segments, particularly of blood vessels and for the treatment and prophylaxis of stenosis, restenosis, arteriosclerosis, atherosclerosis and fibrotic vessel constriction.

Furthermore, catheter balloons which are coated according to the invention are suited for the treatment and/or prophylaxis of in-stent restenosis, i.e. a reoccurring vessel constriction within an already implanted stent in such cases where the placement of an additional stent within an already implanted stent would prove to be very problematic or even impracticable from a medical point of view. Such in-stent restenoses can be effectively treated without an additional stent having to be implanted by applying active agent with the help of a catheter coated according to the present invention or respectively a catheter balloon of a dilatation catheter which balloon is coated according to the present invention.

Furthermore, the catheter balloons coated according to the invention are particularly suited for the treatment of small vessels, preferably such vessels having a vessel diameter of less than 2.25 mm.

The catheter balloons coated according to the invention are preferably used in the cardiovascular area, but the catheter balloons coated according to the invention are also suited for the treatment of vessel constrictions of biliary tracts, esophagus, urinary tracts, pancreas, renal tracts, pulmonary tracts, trachea, small intestine and large intestine.

The following examples illustrate potential embodiments of the invention without limiting the scope of the invention to said precise examples.

EXAMPLES

Example 1a

A commercially available dilatation catheter with expandable balloon composed of a polyamide is provided.

The surface of the catheter balloon is roughened in the range of nanometers to micrometers by means of sand blasting.

Paclitaxel (commercially available from Sigma, Fermentek, BC Biotech or Arianna International) is dissolved in acetone together with shellac at a concentration of 50 µg paclitaxel and 100 µg shellac per ml of acetone.

The solution of paclitaxel and shellac in acetone is sprayed onto the catheter balloon and is repeated three further times after drying the coated balloon surface. The drying process is performed at room temperature and atmospheric pressure.

After the final coating step the catheter balloon is dried under reduced pressure and sterilized with ethylene oxide.

Than the coated balloon surface is protected with a protection cover and packed for shipping or storing.

Example 1b

A commercially available dilatation catheter with expandable balloon composed of a polyamide is provided.

Paclitaxel (commercially available from Sigma, Fermentek, BC Biotech or Arianna International) is dissolved in ethanol together with shellac at a concentration of 50 μg paclitaxel and 100 μg shellac per ml of ethanol.

The solution of paclitaxel and shellac in ethanol is applied onto the catheter balloon with a micropipette.

After the coating step the catheter balloon is dried under reduced pressure and sterilized with ethylene oxide. Than the coated balloon surface is protected with a protection cover and packed for shipping or storing.

Example 1c

A commercially available dilatation catheter with expandable balloon composed of a polyamide is provided.

Paclitaxel (commercially available from Sigma, Fermentek, BC Biotech or Arianna International) is dissolved in ethanol together with shellac at a concentration of 50 μg paclitaxel and 100 μg shellac per ml of ethanol.

The solution of paclitaxel and shellac in ethanol is applied onto the catheter balloon by dipping (dip-coating) the catheter balloon in the solution.

After the coating step the catheter balloon is dried under reduced pressure and sterilized with ethylene oxide. Than the coated balloon surface is protected with a protection cover and packed for shipping or storing.

Example 2

A multifold balloon such as described, for example, in WO 2004/028582 A1, WO 94/23787 A1 or WO 03/059430 A1 is provided. The multifold balloon is provided with a total of 5 folds enclosing a cavity when the balloon is in compressed state and bending outward when it is in expanded state so that the balloon in its expanded state has an essentially tube-like shape.

The multifold balloon is expanded and then its surface is roughened by means of a so called "chemical polishing" process, wherein a suspension of fine particles, preferably in the range of micrometers, is used in said process and said suspension is rubbed onto the surface of the expanded catheter balloon such that a roughened surface is created.

A solution of 80 μg of paclitaxel in 1.0 ml of ethyl acetate and a solution of 100 μg shellac in THF is provided.

The roughened expanded catheter balloon is dipped several times into said solution of paclitaxel in ethyl acetate and dried at room temperature and atmospheric pressure after each dipping.

Than, the shellac solution in THF is filled into a pipette and applied onto the dry paclitaxel coating on the balloon surface.

The total paclitaxel load on the balloon surface is between 1 μg to 5 μg of paclitaxel per mm² of coated balloon surface.

After sterilization, the balloon is provided with a protective sheath intended to protect the active agent on the coated dilatable catheter balloon during transport and storage which sheath is removed prior to the insertion of the catheter by the cardiologist.

Example 3

A commercially available dilatation catheter with expandable balloon made of a polymer is provided. The catheter balloon consists of a block copolymer of polyamide, polyether and polyester or of polyurethane, a polyester or a polyolefin. The balloon surface is smooth and not textured and without channels or cavities.

A solution of 70 μg of paclitaxel and 50 μg of shellac in 1.0 ml of ethanol having a water content of about 3 percent by volume is prepared and applied onto the horizontal area of the surface of the catheter balloon by brushing or spattering.

Subsequently, the catheter balloon is thoroughly dried and sterilized with ethylene oxide. After sterilization, the balloon is provided with a protective sheath intended to protect the active agent on the coated dilatable catheter balloon during transport and storage which sheath is removed prior to the insertion of the catheter by the cardiologist.

Example 4

A coated catheter balloon is manufactured having a paclitaxel coating of 3 μg paclitaxel/mm² balloon surface.

The below described technology is used for the coating of PTCA balloon catheter for application in coronary stenosis. The coating consists of a degradable, drug eluting shellac-paclitaxel composite with a surface loading of normally totaling 4 to 8 μg/mm² whereas the mass portion of paclitaxel component is preferably nominal 1 to 3 μg/mm². This coating layer is applied with intention to release an effectual portion of paclitaxel to the local wall of the artery at the dilated stenosis. Within short term release of paclitaxel during balloon dilatation the convenient effect of the mitosis inhibitor shall combined with fast release of biological biodegradable carrier shellac.

Process Description

1 General Handling:

The complete process of quality assurance, coating and packaging is done under cleanroom similar conditions by using a cytostatic safety cabinet and a laminar flow box.

2 Coating Dilution:

The coating dilution is a mixture of paclitaxel and shellac in proportion 1:1 in a necessary portion of ethyl alcohol. All raw materials undergo an incoming inspection and are defined be raw material specification.

3 Coating Process:

Before coating process the coating quantity must be calculated. The coating quantity is the product of balloon surface and the specific load of 3 μg/mm². After unpacking of the catheter the protection tube must be removed. In cytostatic safety cabinet the catheter will inserted into the working tube and adjusted. After removal of the protection cover the catheter must be inserted to the coating device. Then the catheter would be fixed by a pneumatic actuator and the visual inspection is executed by a microscopical camera. Afterwards the required quantity of coating dilution is applied by a pipette to the distribution rack. The distribution rack is working under influence of a warm air blower until the dilution is distributed at the balloon surface. After evaporation of the ethyl alcohol the coating is fixed with high adhesion at the surface. The postprocessing is done by a drying step with warm air and the visual surface control by microscopical camera.

The coating process is now completed and the catheter must be removed from fixation, the balloon will protected by a protection cover and inserted to the protection tube. The storage of coated devices before packaging is done in a laminar flowbox.

The paclitaxel-shellac coating process is exclusively executed with calibrated and qualified coating equipment and certified raw materials.

The total load of paclitaxel and shellac per mm² balloon surface is 5 µg/mm², while the content of paclitaxel per mm² balloon surface is 1 µg/mm².

4 Packaging Process

The coated PTCA catheters are packaged under laminar flowbox into sterile pouches which are appropriate for ethylene oxide sterilisation. An ethylene oxide indicator is added to every pouch. Afterwards the pouches are labelled in accordance with the order. All following packaging steps are severed from the production area. The EtO sterilization (ethylene oxide sterilization) process is supported by a sterilisation validation.

5 Quality Controls

Both raw materials for coating undergo incoming inspection and will ordered and accepted with certificate. Incoming products will strictly controlled regarding stain, surface defects and scratches by optical inspection. Before and after paclitaxel-shellac coating there is a careful visual surface quality control by microscopical camera. For determination of shellac-paclitaxel coating mass per balloon a differential weight at a dummy sample is installed. This would be done for every new type of balloon size and/or new coating parent solution. The shellac-paclitaxel loading per surface is substantiated by a process validation.

Example 5: Biological Tests

Methods:

1. Location of the Balloon Dilatation:

The locations of the balloon dilatation are presented in Table 1.

2. Porcine Coronary Balloon Dilatation Model:

Seven domestic pigs (weight 18-30 kg) were sedated with 12 mg/kg ketamine hydrochloride, 1 mg/kg xylazine and 0.04 mg/kg atropine after overnight fasting. Loading dose of clopidogrel (300 mg per os) and aspirin (250 mg per os) were administered 24 h prior to procedure. Following intratracheal intubation, arteriotomies of the right femoral arteries were performed under sterile conditions and a 6 F introduction sheath was inserted.

After administration of 200 IU/kg of heparin sodium, selective angiography of the left and right coronary arteries was performed and guide wire was introduced into the distal part of the left anterior descending coronary artery (LAD), left circumflex (LCx) and right coronary arteries (RCA). A paclitaxel-shellac coated balloon catheter (3.0 mm in diameter, 20 mm of length) (Eurocor, Bonn Germany) was inserted into the LAD and LCx after the origin of the first major diagonal branch or the proximal RCA. The paclitaxel-shellac coated balloon was inflated for 30 sec with 709.27-810.59 kPa (7-8 atm), followed by deflation of the balloon, then repeated inflation for 30 sec with 709.27-810.59 kPa (7-8 atm) was performed. Coronary angiography confirmed the occlusion with complete contact of the balloon with the vessel wall in each dilatation. Additionally, in 2 LCx arteries and 1 LAD with relative large obtuse marginalis or diagonal branch (vessel diameter at least 2 mm on the quantitative angiography), bifurcation intervention was performed: first the main branch (MB) was dilated with the inventive paclitaxel-shellac coated balloon 2×30 sec 709.27-810.59 kPa (7-8 atm), then the side branch (SB) with the inventive paclitaxel-shellac coated balloon (2×30 sex, 607.94-810.59 kPa (6-8 atm)) followed by kissing balloon dilatation with the same inventive paclitaxel-shellac coated balloons.

TABLE 1

Location of the paclitaxel-shellac coated balloon dilatation.

| ID (survival time) | LAD MB | LAD SB | LCX MB | LCX SB | RCA Proximal | RCA Distal |
|---|---|---|---|---|---|---|
| PS-balloon-1 (12 h) | PS-balloon 3.0/20 mm | | PS-balloon 3.0/20 mm | PS-balloon 2.5/20 mm | PS-balloon 3.0/20 mm | |
| PS-balloon-2 (12 h) | PS-balloon 3.0/20 mm | PS-balloon 2.5/20 mm | PS-balloon 3.0/20 mm | PS-balloon 2.5/20 mm | PS-balloon 3.0/20 mm | PS-balloon 3.0/20 mm |
| PS-balloon-3 (<1 h) | PS-balloon 3.0/20 mm (mid-LAD) PS-balloon 3.0/20 mm (prox LAD) | | PS-balloon 3.0/20 mm | PS-balloon 2.5/20 mm | | |
| PS-balloon-4 (<1 h) | PS-balloon 3.0/20 mm | PS-balloon 2.5/20 mm | PS-balloon 3.0/20 mm | PS-balloon 2.5/20 mm | PS-balloon 3.0/20 mm | PS-balloon 3.0/20 mm |
| EFFICACY STUDY | | | | | | |
| PS-balloon-5 (2 weeks) | PS-balloon 3.0/20 mm (prox LAD) Allegro 2.5/20 mm (dist LAD) | | PS-balloon 3.0/20 mm (prox LCx) Allegro 2.5/20 mm (dist LCx) | | | |
| PS-balloon-6 (2 weeks) | PS-balloon 3.0/20 mm (prox LAD) Allegro 2.5/20 mm (dist LAD) | | PS-balloon 3.0/20 mm (prox LCx) Allegro 2.5/20 mm (dist LCx) | | | |
| PS-balloon-7 (2 weeks) | PS-balloon 3.0/20 mm (prox LAD) Expleo | | PS-balloon 3.0/20 mm (prox LCx) Allegro | | | |

TABLE 1-continued

| | Location of the paclitaxel-shellac coated balloon dilatation. | | | | | |
|---|---|---|---|---|---|---|
| ID (survival | LAD | | LCX | | RCA | RCA |
| time) | MB | SB | MB | SB | Proximal | Distal |
| | 3.0/20 mm (dist LAD) | | 2.5/20 mm (dist LCx) | | | |

The term PS-balloon refer to the inventive paclitaxel-shellac coated catheter balloon LAD: left anterior descending coronary artery, LCx: left circumflex coronary artery, RCA: right coronary artery The last 3 pigs (PS-balloon 5-7) underwent PS-balloon dilatation of the proximal LAD and LCx arteries (2×30 sec), and distal part of the LAD and LCX were dilated with non-coated balloons. The femoral arteriotomy was repaired and the pigs were allowed to recover.

Euthanasia was performed with saturated potassium chloride approximately 5 min after the last balloon dilatation (PS-balloon-3 and 4) and 12 h later (PS-balloon-1 and 2). Three pigs (PS-balloon-5, 6 and 7) have a follow-up time of 2 weeks (efficacy study). The heart was excised, and the LAD, LCX and RCA dilated coronary arterial segments (orientation after the anatomical landmarks, as side branches, etc) were prepared from the epicardial surface. The dilated arteries of PS-balloon 1-4 were cut with the proximal and distal reference segments (at least 10 mm from the balloon-tip) and were fresh-frozen in liquid nitrogen for determination of the tissue paclitaxel concentrations.

The PS-balloon 5-7 pigs underwent control angiography 2 weeks after balloon dilatation of the left coronary arteries, and then euthanasia was performed. The coronary arteries were prepared and stored in formalin for histomorphometric anaysis and immunohistochemistry.

The experiments were conducted in the Institute of Diagnostics and Oncoradiology, University of Kaposvar, Hungary. "Principle of laboratory animal care" (NIH publication No. 86-23, revised 1985) and the relevant specific Hungarian laws were followed.

3. Measurement of Tissue Paclitaxel Levels:

The paclitaxel concentration of plasma, LAD, LCX, and RCA were measured by HPLC (Anakat Institut für Biotechnologie GmbH, Berlin, Germany). Briefly, after thawing the tissues at ambient temperature they were weighted and depending on the weights different volumes of ethanol were added to the samples (sufficient ethanol to cover the tissue completely). The samples were treated with ultrasound for 40 minutes 200 µl of the samples were centrifuged.

A calibration line was provided in the range between 50 ng/ml up to 5000 ng/ml. The samples for the calibration line were prepared by dilution of a stock solution with a concentration of 1000 µg/ml. An aliquot of all samples (samples from tissue and calibration line) were transferred into autosampler vials and the same volume of 0.1% formic acid was added. The flow rate of the HPLC system was 0.2 ml/min and the column was 0.2 ml/min and the column was ODS Hypersil from ThermoElectron Corporation, particle size 5µ, pore size 120 Å. The isocratic mobile phase consisted of 70% methanol and 30% 0.1% formic acid. Paclitaxel was detected by mass spectrometry operating in MRM-Mode (MRM=multiple reaction monitoring) with a transition of paclitaxel from 854 to 105 AMU.

4. Physical Signs/Symptoms:

The ECG and blood pressure were recorded during the balloon dilatations, and at the follow-up coronary angiography.

5. Quantitative Coronary Angiography in the Efficacy Study:

Pre- and post balloon dilatation, and at the 2 weeks follow up, quantitative angiographic parameters were measured by means of a computer-assisted quantitative coronary arteriographic edge detection algorithm (ACOMPC, Siemens, Germany). In order to minimize variation in the dimensions dependent on the cardiac cycle, end-diastolic frames were chosen for the assessment of pre-, post-dilatation and follow-up minimal lumen (MLD) and reference diameters (RD) and percent diameter stenoses (% DS) of the dilated segments.

6. Histopathology and Histomorphometry of the Dilated Arteries:

Experienced observers have analysed all slides of the coronary arteries, without knowledge of groups. The arterial dilated segments with the distal and proximal reference segments were explanted. Three sections of each arterial segment were stained with hematoxylin-eosin and Verhoeff-van Gieson-elastin to determine the location and extent of injury.

The quantitative analysis included:

Lumen area (area of the vessel lumen, $mm^2$),

Neointima area (area of the neointimal tissue, $mm^2$),

IEL (internal elastic lamina) area (area within the IEL, $mm^2$),

Media area (area of the artery media, $mm^2$),

EEL (external elastic lamina) area (area within the EEL, $mm^2$),

Adventitial area (area of the vessel adventitia, $mm^2$)

Maximal neointimal thickness (at each stent strut site, mm)

Percent area stenosis (neointimal area/IEL area, expressed as percentage, % AS

For each arterial segment, the following histopathological parameters were described: inflammation score (adventitia, media, neointima, overall, score for each: 0-3), fibrinoid/fibrin deposits (score 0-3), haemorrhagia (score 0-3), necrosis (score 0-3), Results:

No alterations in ECG, blood pressures and clinical symptoms were observed during the follow-up. No concomitant disease or fever were recorded.

7. Balloon Implantations:

PS-Balloon-1:

1. Balloon: LAD Mid

PS-balloon 3.0 mm diameter, 20 mm length, balloon inflation pressure 810.59 kPa (8 atm), balloon inflation time: 30 sec and 31 sec, deflation time: 15 sec and 13 sec.

Spasm post balloon dilatation, 1 ml intracoronary nitroglycerine

Final angio: OK

2. Balloon: LCX Mb (Bifurcation)

PS-balloon 3.0 mm diameter, 20 mm length, balloon inflation pressure 810.59 kPa (8 atm), balloon inflation time: 30 sec and 27 sec, deflation time: 15 sec and 10 sec.

No complication during balloon dilatation.

Final angio: OK

3. Balloon: LCX Sb

PS-balloon 2.5 mm diameter, 20 mm length, balloon inflation pressure 607.94 kPa (6 atm), balloon inflation time: 30 sec+30 sec, deflation time: 10 sec+10 sec.

Final kissing balloon dilatation with the same balloons: 30 sec+30 sec

Spasm post balloon dilatation, 1 ml intracoronary nitroglycerine

Final angio: OK

4. Balloon: RCA Prox.

PS-balloon 3.0 mm diameter, 20 mm length, balloon inflation pressure 1013.24 kPa (10 atm), balloon inflation time: 30 sec and 30 sec, deflation time: 5 sec and 5 sec.

No complication during balloon dilatation.

Final angio: OK

PS-Balloon-2:

1. Balloon: LAD Mid (Bifurcation)

PS-balloon 3.0 mm diameter, 20 mm length, balloon inflation pressure 810.59 kPa (8 atm), balloon inflation time: 32 sec+30 sec, deflation time: 10 sec+10 sec.

No complication during balloon dilatation

Final angio: OK

2. Balloon: LAD Diagonal Branch

PS-balloon 2.5 mm diameter, 20 mm length, balloon inflation pressure 810.59 kPa (8 atm), balloon inflation time: 22 sec+22 sec, deflation time: 5 sec+5 sec.

Final kissing balloon dilatation with the same balloons: 30 sec+30 sec

Spasm post balloon dilatation, 1 ml intracoronary nitroglycerine

Final angio: OK

3. Balloon: LCX MB (Bifurcation)

PS-balloon 3.0 mm diameter, 20 mm length, balloon inflation pressure 810.59 kPa (8 atm) and 607.94 kPa (6 atm), balloon inflation time: 25 sec+30 sec, deflation time: 10 sec+10 sec.

No complication during balloon dilatation.

Final angio: OK

4. Balloon: LCX Marginal

PS-balloon 2.5 mm diameter, 20 mm length, balloon inflation pressure 810.59 kPa (8 atm), balloon inflation time: 30 sec (2×), deflation time: 7 sec, 10 sec Final kissing balloon dilatation with the same balloons: 30 sec+30 sec Spasm post balloon dilatation, 1 ml intracoronary nitroglycerine Final angio: OK 5. Balloon: RCA Proximal PS-balloon 3.0 mm diameter, 20 mm length, balloon inflation pressure 1013.24 kPa (10 atm), balloon inflation time: 30 sec+30 sec, deflation time: 5 sec+7 sec.

No complication during balloon dilatation.

Final angio: OK

6. Balloon: RCA Distal

PS-balloon 3.0 mm diameter, 20 mm length, balloon inflation pressure 1013.24 kPa (10 atm), balloon inflation time: 39 sec+30 sec, deflation time: 5 sec+5 sec.

No complication during balloon dilatation.

Final angio: OK

PS-Balloon-3:

1. Balloon: LAD Mid

PS-balloon 3.0 mm diameter, 20 mm length, balloon inflation pressure 810.59 kPa (8 atm), 911.92 kPa (9 atm) balloon inflation time: 30 sec+30 sec, deflation time: 10 sec+10 sec.

No complication during balloon dilatation

Final angio: OK

2. Balloon: LAD Proximal

PS-balloon 3.0 mm diameter, 20 mm length, balloon inflation pressure 810.59 kPa (8 atm), 1013.24 kPa (10 atm) balloon inflation time 30 sec+30 sec: deflation time: 2 sec (2×).

No complication during balloon dilatation.

Final angio: OK

3. Balloon: LCX MB (Bifurcation)

PS-balloon 3.0 mm diameter, 20 mm length, balloon inflation pressure 607.94 kPa (6 atm), balloon inflation time: 30 sec+30 sec, deflation time: 5 sec (2×).

No complication during balloon dilatation.

Final angio: OK

4 Balloon: LCX SB

PS-balloon 2.5 mm diameter, 20 mm length, balloon inflation pressure 607.94 kPa (6 atm), balloon inflation time: 30 sec+30 sec, deflation time: 7 sec and 10 sec Final kissing balloon dilatation with the same balloons: 30 sec+30 sec Spasm post balloon dilatation, 1 ml intracoronary nitroglycerine Final angio: OK PS-balloon-4:

1. Balloon: LCX MB (Bifurcation)

PS-balloon 3.0 mm diameter, 20 mm length, balloon inflation pressure 810.59 kPa (8 atm), balloon inflation time: 30 sec (2×), deflation time: 10 sec No complication during balloon dilatation Final angio: OK 2. Balloon: LCx SB PS-balloon 2.5 mm diameter, 20 mm length, balloon inflation pressure 607.94 kPa (6 atm), balloon inflation time: 30 sec+30 sec, deflation time: 5 sec (2×).

Final kissing balloon dilatation with the same balloons: 30 sec+30 sec

Spasm post balloon dilatation, 1 ml intracoronary nitroglycerine

Final angio: OK

3. Balloon: LAD MB (Bifurcation)

PS-balloon 3.0 mm diameter, 20 mm length, balloon inflation pressure 607.94 kPa (6 atm), balloon inflation time: 30 sec+33 sec deflation time: 5 sec and 5 sec.

Final kissing balloon dilatation with the same balloons: 30 sec+30 sec

No complication during balloon dilatation.

Final angio: OK

4. Balloon: LAD SB Diagonal

PS-balloon 2.5 mm diameter, 20 mm length, balloon inflation pressure 1013.24 kPa (10 atm), 607.94 kPa (6 atm) balloon inflation time: 30 sec+30 sec, deflation time: 5 sec and 5 sec Final kissing balloon dilatation with the same balloons: 30 sec+30 sec Spasm post balloon dilatation, 1 ml intracoronary nitroglycerine
Final angio: OK
5. Balloon: RCA Distal
PS-balloon 3.0 mm diameter, 20 mm length,
balloon inflation pressure 911.92 kPa (9 atm), balloon inflation time: 30 sec+30 sec, deflation time: 5 sec+7 sec.
No complication during balloon dilatation.
Final angio: OK
6. Balloon: RCA Proximal
PS-balloon 3.0 mm diameter, 20 mm length,
balloon inflation pressure 810.59 kPa (8 atm), balloon inflation time: 29 sec+30 sec, deflation time: 5 sec+5 sec.
No complication during balloon dilatation.
Final angio: OK
PS-balloon-5:
1. Balloon: LCX Proximal
PS-balloon 3.0 mm diameter, 20 mm length,
balloon inflation pressure 911.92 kPa (9 atm) balloon inflation time: 30 sec+30 sec, deflation time: 5 sec
No complication during balloon dilatation
Final angio: OK
2. Balloon: LCX Distal
Allegro 2.5 mm diameter, 20 mm length,
balloon inflation pressure 810.59 kPa (8 atm) and 607.94 kPa (6 atm), balloon inflation time: 30 sec+30 sec, deflation time: 11 sec.
Spasm post balloon dilatation, 2×1 ml intracoronary nitroglycerine
Final angio: OK
3. Balloon: LAD Proximal
PS-balloon 3.0 mm diameter, 20 mm length,
balloon inflation pressure 810.59 kPa (8 atm), balloon inflation time: 30 sec+30 sec deflation time: 5 sec.
No complication during balloon dilatation.
Final angio: OK
4. Balloon: LAD Distal
Allegro 2.5 mm diameter, 20 mm length,
balloon inflation pressure 607.94 kPa (6 atm) balloon inflation time: 30 sec+30 sec, deflation time: 13 sec
No complication during balloon dilatation.
Final angio: OK
PS-balloon-6:
1. Balloon: LCX Proximal
PS-balloon 3.0 mm diameter, 20 mm length,
balloon inflation pressure 810.59 kPa (8 atm) balloon inflation time: 30 sec+30 sec, deflation time: 5 sec
No complication during balloon dilatation
Final angio: OK
2. Balloon: LCX Distal
Allegro 2.5 mm diameter, 20 mm length,
balloon inflation pressure 607.94 kPa (6 atm), balloon inflation time: 30 sec+30 sec, deflation time: 10 sec.
No complication during balloon dilatation.
Final angio: OK
3. Balloon: LAD Proximal
PS-balloon 3.0 mm diameter, 20 mm length,
balloon inflation pressure 810.59 kPa (8 atm), balloon inflation time: 30 sec+30 sec deflation time: 5 sec.
No complication during balloon dilatation.
Final angio: OK
4. Balloon: LAD Distal
Allegro 2.5 mm diameter, 20 mm length,
balloon inflation pressure 607.94 kPa (6 atm) balloon inflation time: 30 sec+30 sec, deflation time: 10 sec Spasm post balloon dilatation, 2×1 ml intracoronary nitroglycerine, 5000 IU Heparin ic
Final angio: OK
PS-balloon-7:
1. Balloon: LCX Proximal
PS-balloon 3.0 mm diameter, 20 mm length,
balloon inflation pressure 810.59 kPa (8 atm) balloon inflation time: 30 sec+30 sec, deflation time: 5 sec
No complication during balloon dilatation
Final angio: OK
2. Balloon: LCX Distal
Allegro 2.5 mm diameter, 20 mm length,
balloon inflation pressure 810.59 kPa (8 atm) and 607.94 kPa (6 atm), balloon inflation time: 30 sec+30 sec, deflation time: 12 sec.
No complication during balloon dilatation.
Final angio: OK
3. Balloon: LAD Proximal
PS-balloon 3.0 mm diameter, 20 mm length,
balloon inflation pressure 810.59 kPa (8 atm), balloon inflation time: 30 sec+30 sec deflation time: 5 sec.
No complication during balloon dilatation.
Final angio: OK
4. Balloon: LAD Distal
Expleo 3.0 mm diameter, 20 mm length,
balloon inflation pressure 405.29 kPa (4 atm) balloon inflation time: 30 sec+30 sec, deflation time: 12 sec
No complication during balloon dilatation.
Final angio: OK
8. Tissue Paclitaxel Concentration:

The tissue paclitaxel concentration was very high, in some bifurcation over 1000 uM/L. The calibration curve and the tissue probes have been controlled, but no mistake in measurements were found. Some other parallel measured tissues contained very small amount of paclitaxel, which confirmed the accuracy of the measurements. Furthermore, 5 samples have been sent 1 week later, they have shown similar high concentration of paclitaxel with the new calibration curve. Table 2 presents the mean and standard deviations of the values in single vessel and bifurcation dilatation.

There were large scattering of the data, but the data are consequent; as the values are lower at 12 h as compared with the values at 45 min, and the bifurcation values are 2-3× higher than the single vessel values (Table 2).

TABLE 2

Coronary artery tissue paclitaxel concentration after balloon dilatation with the inventive paclitaxel-shellac coated catheter balloon.

| Tissue paclitaxel concentration (µM/L) Single vessel | Time after balloon dilat. Mean 45 min (n = 4) | Time after balloon dilat. Mean 12 h (n = 4) |
| --- | --- | --- |
| Dilated segment (µM/L) | 184.4 ± 178.4 | 39.3 ± 48.7 |
| Proximal reference segment | 111.0 ± 79.5 | 38.8 ± 74.3 |
| Distal reference segment (µM/L) | 62.1 ± 77.3 | 38.1 ± 33.1 |
| Bifurcation | (n = 3) | (n = 3) |
| Bifurcation main branch (µM/L) | 498.1 ± 339.9 | 267.8 ± 297.3 |
| Bifurcation main branch proximal reference segment (µM/L) | 196.2 ± 320.4 | 161.2 ± 139.8 |
| Bifurcation main branch distal reference segment (µM/L) | 224.5 ± 170.4 | 100.0 ± 134.1 |
| Bifurcation side branch (µM/L) | 220.7 ± 306.4 | 26.1 ± 42.1 |
| Bifurcation side branch distal reference segment (µM/L) | 42.1 ± 61.7 | 37.0 ± 63.5 |

Example 6: Biological Tests II

Animal Preparation

After overnight fasting, 33 domestic pigs (weight 18-30 kg) were premedicated with intramuscular injection of 12 mg/kg ketamine hydrochloride, 1 mg/kg xylazine and 0.04 mg/kg atropine. The anesthesia was deepened with isofluran and $O_2$ via a mask, followed by intratracheal intubation. The anesthesia was maintained with 1.5-2.5 vol % isofluran, 1.6-1.8 vol % $O_2$ and 0.5 vol % $N_2O$. $O_2$ saturation. Blood pressure and electrocardiogram were monitored continuously. Arteriotomies of the right femoral arteries were performed under sterile conditions, and a 6F introduction sheath was inserted. After administration of 200 IU/kg of heparin sodium, selective angiography of the left and right coronary arteries were performed and a guide-wire was introduced into the distal part of the left anterior descending (LAD) and left circumflex (LCx) coronary arteries. The balloon catheters (2.75-3.0 mm in diameter, 15 mm in length) were inserted into the LAD past the origin of the first major diagonal branch, and into LCx beyond the origin of the first marginal branch, and balloon dilation was performed. Coronary angiography confirmed the full contact of the balloon with the vessel wall during each balloon inflation. The inflation time was chosen in accordance with the protocol, e.g. either the safety or the efficacy phase of the study. The animals were then euthanized for the safety study or allowed to recover for the efficacy study. The experiments were conducted in the Institute of Diagnostics and Oncoradiology, University of Kaposvar, Hungary. The animal investigations conform to the "Position of the American Heart Association on Research Animal Use", adopted by the AHA on Nov. 11, 1984, and the relevant specific Hungarian laws were followed.

Local Drug Delivery Device

The DIOR Paclitaxel-shellac catheter balloon (Eurocor GmbH) is a coronary dilation balloon for human use with a 3.0 $\mu g/mm^2$ balloon-surface paclitaxel-shellac coating. The drug is dissolved in shellac, which is composed of a network of hydroxy fatty acid esters and sesquiterpene acid esters with a molecular weight of about 1000; aleuritic acid and jalaric acid and/shelloic acid are the major constituents of shellac.

The 1:1 mixture of paclitaxel and shellac is coated onto the microporous DIORballoon-surface structure. During the insertion of the DIOR Paclitaxel-shellac catheter balloon (Eurocor GmbH) and tracking to the coronary lesion, the three-folded DIOR Paclitaxel-shellac catheter balloon protects the loaded drug from an early wash-off effect.

Safety Study

For measurements of tissue paclitaxel concentration after balloon inflation, the DIOR Paclitaxel-shellac catheter balloon (Eurocor GmbH) was inserted into the LAD and LCx. To assess the increase in tissue Paclitaxel concentrations as a function of balloon inflation times, the DIOR Paclitaxel-shellac catheter balloons were inflated for 15 s in 10 coronary segments, for 20 s in 6 coronary segments, for 30 s in 6 coronary segments, for 45 s in 7 coronary segments and 2×30 sec in 6 coronary segments and at 607.94-1418.53 kPa (6-14 atm) (1.3:1 balloon/artery ratio). Blood samples were taken 5, 10 and 30 min after balloon inflation. Euthanasia was performed with saturated potassium chloride at 45 min or 12 h after DIOR Paclitaxel-shellac catheter balloon (Eurocor GmbH) inflation. The balloons were then stored for measurements of remnant surface paclitaxel amount. The LAD and LCx dilated coronary arterial segments were prepared with additional proximal and distal reference segments (max. 10 mm proximal or distal from the dilated segment), and fresh-frozen for determination of tissue paclitaxel concentrations. Tissue samples (connective tissue, fat and myocardium), 1, 2 and 3 mm beneath the artery were prepared for determination of the depth of vertical paclitaxel penetration into the tissue.

Measurement of Tissue, Balloon Surface and Plasma Paclitaxel Concentrations

The paclitaxel concentration in the artery walls, the underlying tissue at 1, 2 and 3 mm deep layers, balloon surface and plasma was measured by high-performance liquid chromatography (HPLC). After thawing, the tissues were weighed at ambient temperature and, depending on weight different volumes of ethanol were added to the samples (sufficient ethanol to cover the tissue completely). The samples were then treated with ultrasound for 40 min, and 200-μL aliquots were then centrifuged and stored for subsequent measurements. A calibration line was produced in the range between 50 and 5000 ng/mL. The samples for the calibration line were prepared by dilution of a stock solution with a concentration of 1000 μg/mL. Aliquots of all samples (samples from tissue and calibration line) were transferred into auto-sampler vials and the same volume of 0.1% formic acid was added. The flow rate of the HPLC system was 0.2 mL/min through a column of ODS Hypersil (ThermoElectron Corporation), particle size 5μ, pore size 120 Å. The isocratic mobile phase consisted of 70% methanol and 30% 0.1% formic acid. Paclitaxel was detected by mass spectrometry in multiple reaction monitoring mode with a transition of paclitaxel from 854 to 105 AMU. The tissue paclitaxel concentration was expressed in μM/L, which measure is independent from the sample weight. The plasma paclitaxel amount was given in ng/mL.

Efficacy Study

The neointimal proliferation caused by balloon overstretch injury (1.3:1 balloon/artery ratio) was compared using uncoated AMADEUS Supercross catheter balloon (n=6) or DIOR Paclitaxel-shellac catheter balloon (n=6) in the LAD and LCx. Loading dose of clopidogrel (300 mg per os) and acetylsalicylic acid (250 mg per os) were administered 24 h prior to the procedure. The medication was continued with a daily dose of 75 mg clopidogrel and 100 mg acetylsalicylic acid during the 2-week follow-up (FUP). Each pig was treated with both uncoated AMADEUS Supercross catheter balloon and DIOR Paclitaxel-shellac catheter balloon in a randomized fashion (DIOR Paclitaxel-shellac catheter balloon in either LAD or LCx). The balloons (2.75-3 mm of diameter, 15 mm of length) were inflated with 1013.24-1823.84 kPa (10-18 atm) for 30 s in order to achieve the 1.3:1 balloon:artery ratio. Control angiography was performed at 2-week FUP, followed by euthanasia. For histopathological and histomorphometric analyses, the coronary arteries were flushed with 100 ml saline followed by pressure fixation in 4% buffered formaldehyde for 30 min at 100-110 mmHg. The arteries were then cut from the epicardial surface and the location of the previous dilation was carefully identified based on the anatomical landmarks (side branches). The dilated segment (divided into three sections, such as proximal, mid and distal dilated segments), the proximal and distal reference segments (max. 10 mm proximal or distal from the dilated segment) were then fixed in 2% buffered formalin. Following this preparation, the arterial sections were embedded in paraffin and cut into 4-6-μm-thick slices and routinely stained with hematoxylin-eosin and Verhoeff-van Gieson-elastin.

Histopathology and Histomorphometry of the Arteries 2 Weeks after Overstretch Injury The histological analysis was performed by experienced investigators blinded to the treatments and focused on the arterial injury, and measurements of the neointimal hyperplasia. The following histopathological parameters were measured: injury score, fibrin and inflammation scores, and endothelialization. Vessel injury was determined by the anatomic vessel structures similar to the injury score after stenting (Schwartz et al., J Am Coil Cardiol, 1992, 19, 267-74), and adapted for balloon injury only (Rosenthal et al., Circulation, 2001, 104, 2222-2227). A numeric value was assigned according to the of severity injury: Grade 0: (no injury): internal (IEL) and external elastic lamina (IEL) and media intact; Grade 0.05: IEL minimal disruption, media and EEL intact; Grade 1: IEL lacerated, media and EEL intact; Grade 1.5 IEL lacerated, media<half thickness lacerated, EEL intact; Grade 2: IEL lacerated, media>half thickness lacerated, EEL intact; Grade 2.5: IEL and media (full thickness) lacerated, IEL minimal disruption; Grade 3: IEL, media (full thickness) and EEL lacerated. Inflammation score was graded as 0 for no inflammation to minimal amount of interspersed inflammatory cells in media or adventitia; 1 for mild inflammatory infiltration or focally moderated in <25% of the vessel area in media or adventitia; 2 for moderate inflammatory infiltration or focally marked in 25-50% of the vessel area in media or adventitia; 3 for heavy inflammatory infiltration or focally marked in >50% of the vessel area in media or adventitia, and 4 for granulomatous inflammatory reaction in any layer of the artery. Fibrin score was graded from 0 to 3 as no fibrin deposition or mild, moderate or heavy fibrin deposition, involving <10%, 10-25% or >25% of the circumference of the vessel, respectively. Endothelialization was evaluated with a score system comprising absent, partial or complete. The following quantitative histomorphometric parameters of the dilated segment, and proximal and distal reference segments were measured: 1) lumen area, 2) IEL area, 3) EEL area, and 4) maximal neointimal thickness. The calculated histomorphometric parameters were as follows: 1) neointima area (difference between IEL and lumen area), 2) media area (difference between EEL and IEL area), 3) % area stenosis ((neointimal area/IEL area)*100), 3) remodeling index (EEL area of the dilated arterial segment/EEL area of the proximal reference segment Tissue Distribution of Paclitaxel Using Paclitaxel-Eluting Stent and DIOR Paclitaxel-Shellac Catheter Balloon Tissue distribution of paclitaxel after coronary intervention with fluorescent-paclitaxel (Oregon Green 488 Fluorecent paclitaxel conjugate, Molecular Probes, Invitrogen, Paisley PA4 9RF, UK) conjugate-coated stent and DIOR catheter balloon (both 3.0 mm in size and 15 mm in length, balloon inflation time 30 s with 1013.24 kPa (10 atm)) was compared. The arteries were prepared from the epicardial surface. The stent was removed carefully, and the arteries were cut longitudinally and unfolded. The intimal surface was displayed with fluorescent microscopy.

Results

There was no procedural or post-procedural complication after the use of the DIOR Paclitaxel-shellac catheter balloon for dilation of the coronary arteries. Safety study Paclitaxel concentrations in arterial tissue 45 min and 12 h post-dilation increased with increasing duration of balloon inflation times (15, 20, 30 and 45 s) reaching a plateau with 30 s (FIG. 1), with no further increase even after 60 s inflation time. The measured arterial tissue paclitaxel concentrations were 29±3 µM/L, 52±6 µM/L, 196±44 µM/L, 202±36 µM/L and 184±59 µM/L after 15, 20, 30, 45 and 60 s of inflation, respectively, 45 min after exposure of the artery with the drug. Paclitaxel concentrations were also detected in proximal and distal reference segments (FIG. 1). There were gradually decreasing remnant amount of paclitaxel on the balloon surfaces after balloon inflation times of 15 (182±12 µg), 20 (144±10 µg), 30 (131±12 µg), 45 (85±4 µg) and 60 (73±6 µg) s with an 75±7 and 81±6% drug release from the balloon surface after a balloon inflation duration of 30 or 45 s, respectively. The arterial tissue paclitaxel concentration decreased up to 1±0.1 µM/L, 31±3 µM/L, 50±8 µM/L, 47±9 µM/L and 48±7 µM/L 12 h post-dilation, according to increasing balloon inflation time (FIG. 1). The tissues beneath the arteries contained Paclitaxel in increasing amount up to 60 s inflation time at 1 and 2 mm vertical deepness 45 min postdilation (FIG. 2), with maximal paclitaxel concentrations of 12.4±3.2 and 7.3±1.9 µM/L respectively, while no paclitaxel was detected at 3 mm deepness. Paclitaxel concentrations in plasma (up to 85.8 ng/mL; mean 45±28 ng/mL) were only detectable after a balloon inflation time of 60 s, 5 min post exposure. Ten min after DIOR Paclitaxel-shellac catheter balloon use, no paclitaxel could be measured in plasma, even not after 60 sec balloon inflation time.

Efficacy Study

Two weeks post-overstretch injury, histopathological analyses revealed similar fibrin score and injury score in the groups. The inflammation score was somewhat higher in the uncoated AMADEUS Supercross catheter balloon group, without significant difference between the groups (FIG. 3). No giant cells or granulomatous reaction was found in either group. The endothelialization was complete in both groups. Histomorphometry showed significant smaller neointimal hyperplasia and neointimal thickness in the DIOR Paclitaxel-shellac catheter balloon group compared to the uncoated AMADEUS Supercross catheter balloon group (FIG. 4). Consequently, lumen area in the coronary arteries increased and was larger in the DIOR Paclitaxel-shellac catheter balloon compared to the uncoated AMADEUS Supercross catheter balloon (FIG. 5). No relevant vessel remodeling was found in any of the groups (FIG. 3).

Tissue Distribution of Paclitaxel

Fluorescence paclitaxel derivative-coating of DIOR balloon showed a homogenous distribution of the drug onto the vessel, in contrast with the uneven distribution caused by the fluorescence paclitaxel derivative-coated stent.

REFERENCE LIST

1. Lumen
2. Neointima
3. Internal elastic lamina
4. Media
5. External elastic lamina

Figure 1:
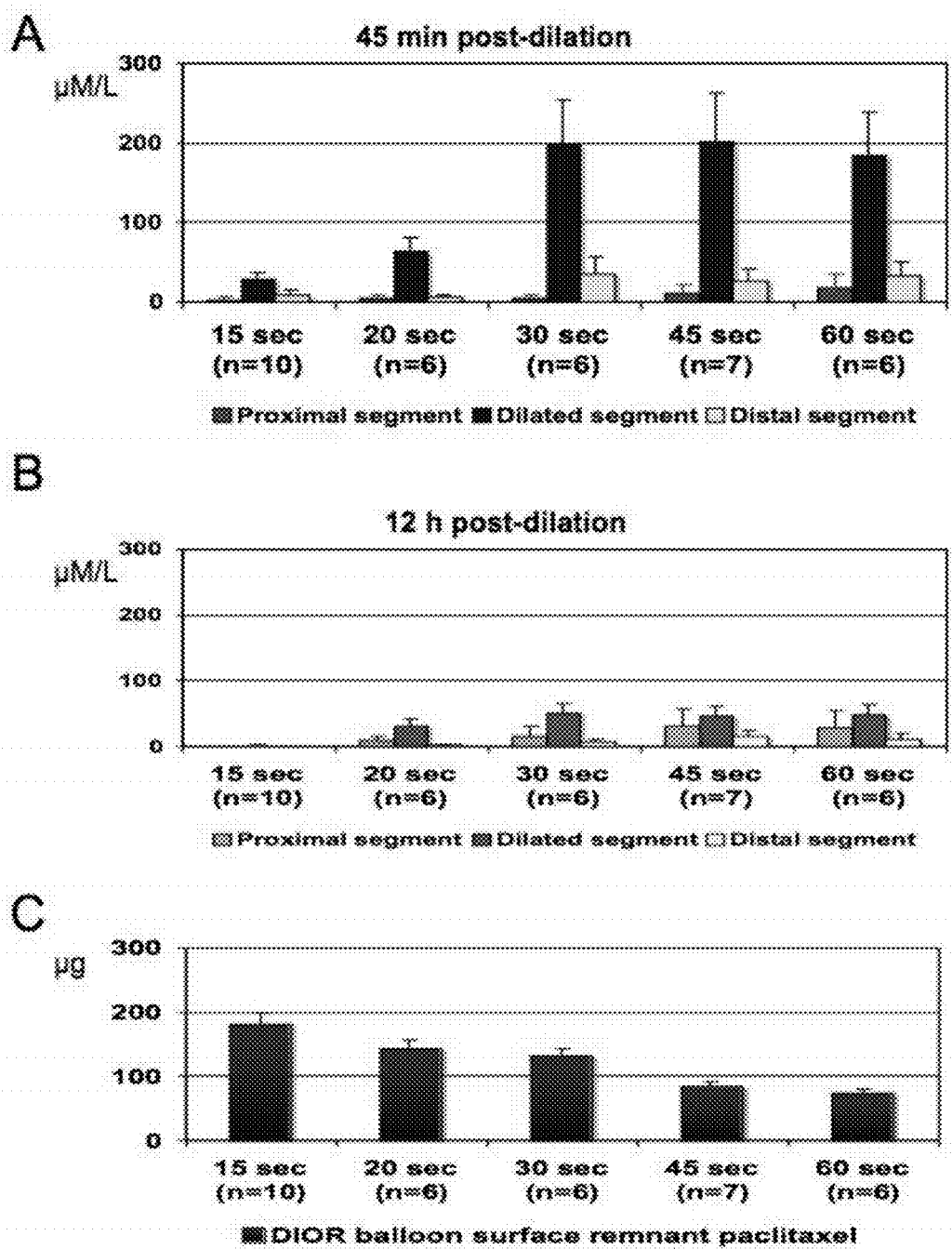
FIG. 1

Inflation time-dependent tissue and balloon surface paclitaxel concentrations DIOR Paclitaxel-shellac coated catheter balloons were dilated in coronary artery tissue for 15 s, 20 s, 30 s, 45 s and 60 s. The Paclitaxel concentration in the proximal-, dilated-, and distal segment was measured after 45 min post-dilation (A) or after 12 h post-dilation (B) and is displayed in µM/L. The remaining Paclitaxel on the surface of the catheter balloons after 15 s, 20 s, 30 s, 45 s and 60 s inflation was measured and is displayed in µg (C).

A. Coronary artery tissue paclitaxel concentrations of dilated segments (middle bar), proximal segments (left bar) as well as distal reference segments (right bar) measured 45 min after 15, 20, 30, 45 and 60 s balloon inflations.
B. Coronary artery tissue paclitaxel concentrations of dilated segments (middle bar), proximal segments (left bar) as well as distal reference segments (right bar) measured 12 h after 15, 20, 30, 45 and 60 s balloon inflations.
C. Remnant paclitaxel amount of the balloon surface, after 15, 20, 30, 45 and 60 s balloon inflations.
FIG. 2

Inflation time-dependent tissue and plasma paclitaxel concentrations DIOR Paclitaxel-shellac coated catheter balloons were dilated in coronary artery tissue for 15 s, 20 s, 30 s, 45 s and 60 s and the vertical penetration (A) as well as the plasma Paclitaxel concentration was measured (B).
A. Vertical penetration of the paclitaxel at 1 mm (left bar) and 2 mm (right bar) deepness depending on balloon inflation time measured at 45 min post-dilation.
B. Plasma paclitaxel concentration 5 min post-balloon inflation. Paclitaxel could be measured only 60 s balloon inflation time. No paclitaxel was detected 10 min postdilation (not shown).
FIG. 3

Figure 4:
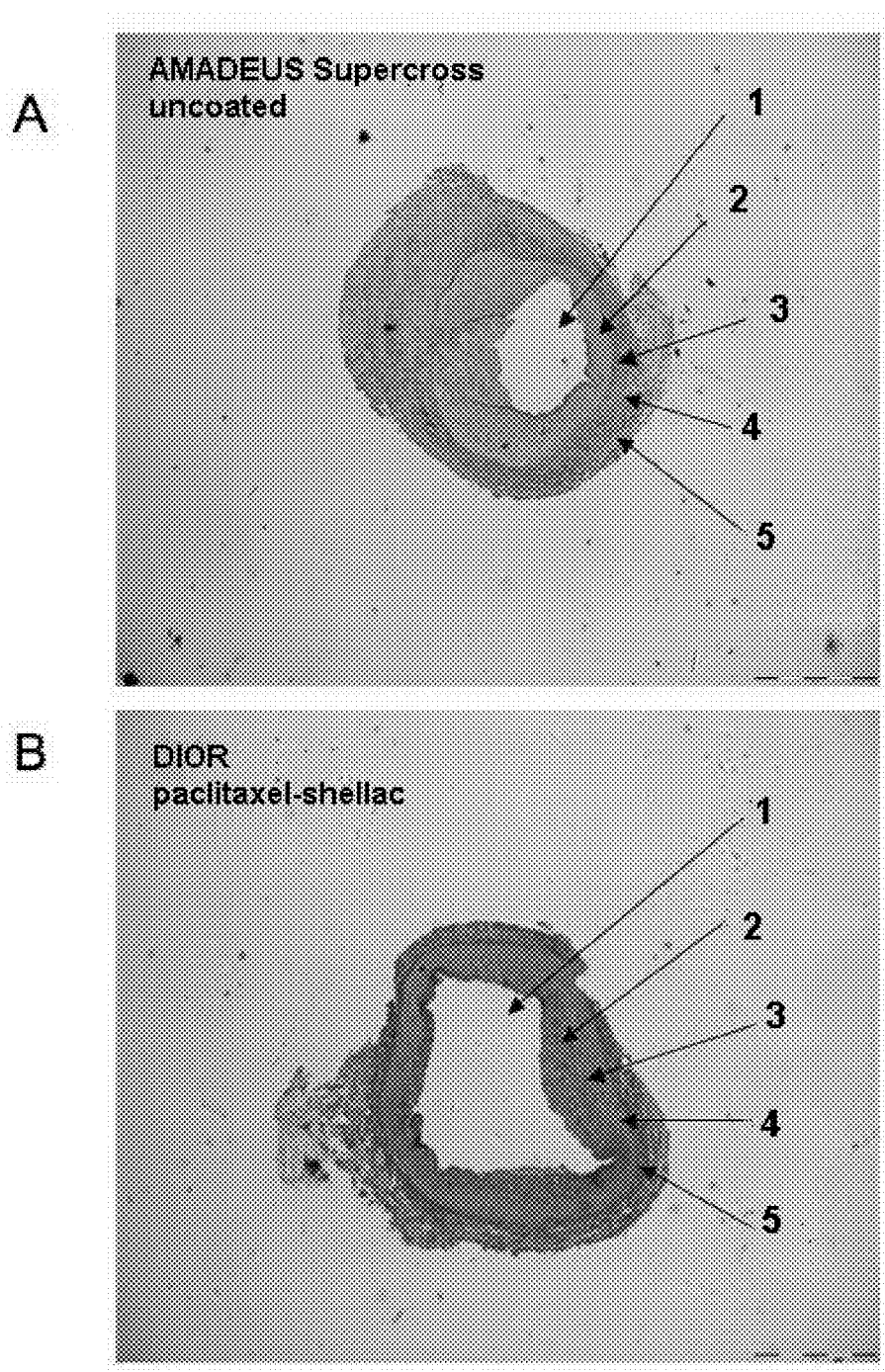

Histomorphometric parameter of dilated arteries 2 weeks post-balloon dilatation with uncoated AMADEUS Supercross catheter balloon or DIOR Paclitaxel-shellac catheter balloon. A dilatation time of 30 seconds was used.
FIG. 4

Histology of overstretch injury after DIOR Paclitaxel-shellac catheter balloon or uncoated AMADEUS Supercross catheter balloon use Representative histologic slides 2 weeks after balloon overstretch injury with conventional (A) or DIOR Paclitaxel-shellac catheter balloon (B) balloon.
FIG. 5

Differences between the DIOR Paclitaxel-DMSO catheter balloon and DIOR Paclitaxel-shellac catheter balloon

What is claimed is:

1. A method for coating a catheter balloon comprising the following steps:
  I) providing an uncoated catheter balloon; and
  IIA) providing a solution of paclitaxel and shellac; or
  IIB) providing a solution of paclitaxel and providing a solution of shellac; and
  IIIA) coating the surface of the catheter balloon with the solution of paclitaxel and shellac; or
  IIIB) coating the surface of the catheter balloon with the solution of paclitaxel and subsequently with the solution of shellac or coating the surface of the catheter balloon with the solution of shellac and subsequently with the solution of paclitaxel;
  IV) drying the coated catheter balloon.

2. The method according to claim 1, wherein the solution of paclitaxel and the solution of shellac or the solution of paclitaxel and shellac are prepared in acetone, ethyl acetate, ethanol, methanol, DMSO, THF, chloroform, methylene chloride or mixtures of the afore-mentioned solvents.

3. The method according to claim 2, wherein the solution of paclitaxel and shellac IIA) or the solution of paclitaxel IIB) has a paclitaxel content that is between 10 to 500 µg of paclitaxel per 1 ml solution.

4. The method according to claim 1, wherein the total surface loading with paclitaxel and shellac of the catheter balloon is between 1 µg/mm² and 12 µg/mm² and/or wherein the total surface loading with paclitaxel of the catheter balloon is between 0.5 µg/mm² and 6 µg/mm².

5. The method according to claim 1 further comprising the step of protecting any parts of the balloon catheter which should not be coated with a removable protection sheet.

6. The method according to claim 1 further comprising the step V):
  V) Protecting the coated catheter balloon with a removable protection cover.

7. The method according to claim 1, wherein at least one carrier substance is added to the solution of paclitaxel and shellac IIA), or the solution of paclitaxel IIB).

8. The method according to claim 7, wherein the at least one carrier substance is selected from the group consisting of:
  parylene C, parylene D, parylene N, parylene F, polyvalerolactones, poly-ε-decalactone, polylactonic acid, polyglycolic acid, polylactides, polyglycolides, copolymers of the polylactides and polyglycolides, poly ε-caprolactone, polyhydroxybutyric acid, polyhydroxybutyrates, polyhydroxyvalerates, polyhydroxybutyrate-co-valerate, poly(1,4-dioxane-2,3-dione), poly(1,3-dioxane-2-one), poly-para-dioxanone, polyanhydrides, polymaleic acid anhydride, polyhydroxymethacrylates, fibrin, polycyanoacrylate, polycaprolactone dimethylacrylates, poly-B-maleic acid, polycaprolactone butyl acrylates, multiblock polymers from oligocaprolactonedioles and oligodioxanonedioles, polyether ester multiblock polymers from PEG and poly(butylene terephthalate), polypivotolactones, polyglycolic acid trimethyl carbonates, polycaprolactone glycolides, poly(γ-ethyl glutamate), poly(DTH-iminocarbonate), poly(DTE-co-DT-carbonate), poly(bisphenol A-iminocarbonate), polyorthoesters, polyglycolic acid trimethyl-carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoi c acid, polyanhydrides, polyethylene oxide propylene oxide soft polyurethanes, polyurethanes having amino acid residues in the backbone, polyether esters, polyethylene oxide, polyalkene oxalates, polyorthoesters as well as their copolymers, lipids, carrageenans, fibrinogen, starch, collagen, polyamino acids, synthetic polyamino acids, zein, polyhydroxyalkanoates, pectic acid, actinic acid, carboxymethyl sulfate, albumin, hyaluronic acid, chitosan and derivatives thereof, heparan sulfates and derivatives thereof, heparins, chondroitin sulfate, dextran, B-cyclodextrins, copolymers with PEG and polypropylene glycol, gum arabic, guar, gelatin, collagen N-hydroxysuccinimide, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylene, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM gums, fluorosilicones, carboxymethyl chitosans, polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, silicones, polysiloxanes, polydimethylsiloxanes, polyvinyl halogens and copolymers, cellulose ethers, cellulose triacetates, chitosans and copolymers of chitosans, and/or mixtures of the aforementioned polymers.

9. The method according to claim 1, wherein steps IIIA) or IIIB) and IV) are repeated several times.

10. The method according to claim 1, wherein the solution of paclitaxel and shellac IIA), or the solution of paclitaxel IIB), has a paclitaxel content that is between 10 to 500 µg of paclitaxel per 1 ml solution.

11. The method according to claim 1, wherein the solution of paclitaxel and shellac IIA), or the solution of paclitaxel IIB), is applied by one or more from the group consisting of spray coating, brush coating, dip coating, vapour deposition or pipetting.

12. The method according to claim 1, wherein the catheter balloon consists of a material or a mixture of materials, wherein the material or the mixture of materials is selected from the following group of materials consisting of:

parylene C, parylene D, parylene N, parylene F, polyvalerolactones, poly-ε-decalactone, polylactonic acid, polyglycolic acid, polylactides, polyglycolides, copolymers of the polylactides and polyglycolides, poly ε-caprolactone, polyhydroxybutyric acid, polyhydroxybutyrates, polyhydroxyvalerates, polyhydroxybutyrate-co-valerate, poly(1,4-dioxane-2,3-dione), poly(1,3-dioxane-2-one), poly-para-dioxanone, polyanhydrides, polymaleic acid anhydride, polyhydroxymethacrylates, fibrin, polycyanoacrylate, polycaprolactone dimethylacrylates, poly-B-maleic acid, polycaprolactone butyl acrylates, multiblock polymers from oligocaprolactonedioles and oligodioxanonedioles, polyether ester multiblock polymers from PEG and poly(butylene terephthalate), polypivotolactones, polyglycolic acid trimethyl carbonates, polycaprolactone glycolides, poly(γ-ethyl glutamate) poly(DTH-iminocarbonate), poly(DTE-co-DT-carbonate), poly(bisphenol A-iminocarbonate), polyorthoesters, polyglycolic acid trimethyl-carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoi c acid, polyanhydrides, polyethylene oxide propylene oxide, soft polyurethanes, polyurethanes having amino acid residues in the backbone, polyether ester, polyethylene oxide, polyalkene oxalates, polyorthoesters as well as their copolymers, lipids, carrageenans, fibrinogen, starch, collagen, polyamino acids, synthetic polyamino acids, zein, polyhydroxyalkanoates, pectic acid, actinic acid, carboxymethyl sulfate, albumin, hyaluronic acid, chitosan and derivatives thereof, heparan sulfates and derivatives thereof, heparins, chondroitin sulfate, dextran, β-cyclodextrins, copolymers with PEG and polypropylene glycol, gum arabic, guar, gelatine, collagen N-hydroxysuccinimide, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylene, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM gums, fluorosilicones, carboxymethyl chitosans, polyaryletheretherketones, polyetheretherketones, polyethylene terephthalate, polyvalerates, carboxymethylcellulose, cellulose, rayon, rayon tri acetates, cellulose nitrates, cellulose acetates, hydroxyethyl cellulose, cellulose butyrates, cellulose acetate butyrates, ethyl vinyl acetate copolymers, polysulfones, epoxy resins, ABS resins, silicones, polysiloxanes, polydimethylsiloxanes, polyvinyl halogens and copolymers, cellulose ethers, cellulose triacetates, chitosans as well as copolymers of chitosans, and/or mixtures of the aforementioned polymers.

13. The method according to claim 1, wherein an additional active agent is added to the paclitaxel and/or shellac containing solution and wherein said additional active agent is selected from the group consisting of:

abciximab, acemetacin, acetylvismione B, aclarubicin, ademetionine, adriamycin, aescin, afromosone, akagerine, aldesleukin, amidorone, aminoglutethimide, amsacrine, anakinra, anastrozole, anemonin, anopterine, antimycotics antithrombotics, apocymarin, argatroban, aristolactam-AII, aristolochic acid, ascomycin, asparaginase, aspirin, atorvastatin, auranofin, azathioprine, azithromycin, baccatin, bafilomycin, basiliximab, bendamustine, benzocaine, berberine, betulin, betulinic acid, bilobol, bisparthenolidine, bleomycin, combrestatin, Boswellic acids and derivatives thereof, bruceanol A, B and C, bryophyllin A, busulfan, antithrombin, bivalirudin, cadherins, camptothecin, capecitabine, o-carbamoyl-phenoxyacetic acid, carboplatin, carmustine, celecoxib, cepharanthin, cerivastatin, CETP inhibitors, chlorambucil, chloroquine phosphate, cicutoxin, ciprofloxacin, cisplatin, cladribine, clarithromycin, colchicine, concanamycin, a warfarin, C-type natriuretic peptide, cudraisoflavone A, curcumin, cyclophosphamide, ciclosporin A, cytarabine, dacarbazine, daclizumab, dactinomycin, dapsone, daunorubicin, diclofenac, 1,11-dimethoxycanthin-6-one, docetaxel, doxorubicin, daunamycin, epirubicin, epothilone A and B, erythromycin, estramustine, etoposide, everolimus, filgrastim, fluroblastin, fluvastatin, fludarabine, fludarabine-5'-dihydrogen phosphate, fluorouracil, folimycin, fosfestrol, gemcitabine, ghalakinoside, ginkgol, ginkgolic acid, glycoside 1a, 4-hydroxyoxycyclo phosphamide, idarubicin, ifosfamide, josamycin, lapachol, lomustine, lovastatin, melphalan, midecamycin, mitoxantrone, nimustine, pitavastatin, pravastatin, procarbazine, mitomycin, methotrexate, mercaptopurine, thioguanine, oxaliplatin, irinotecan, topotecan, hydroxycarbamide, miltefosine, pentostatin, pegaspargase, exemestane, letrozole, formestane, mycophenolate mofetil, β-lapachone, podophyllotoxin, podophyllic acid-2-ethyl hydrazide, molgramostim, peginterferon α-2b, lenograstim, macrogol, selectin, cytokinin inhibitors, COX-2 inhibitor, angiopeptin, monoclonal antibodies inhibiting muscle cell proliferation, bFGF antagonists, probucol, prostaglandins, 1-hydroxy-11-methoxycanthin-6-one, scopoletin, NO donors, pentaerythrityl tetranitrate and sydnoimines, S-nitroso derivatives, tamoxifen, staurosporine, β-estradiol, α-estradiol, estriol, estrone, ethinyl estradiol, medroxyprogesterone, estradiol cypionates, estradiol benzoates, tranilast, kamebakaurin and other terpenoids used in cancer therapy, verapamil, tyrosine kinase inhibiotors, paclitaxel and derivatives thereof, 6-a-hydroxy-paclitaxel, docetaxel, mofebutazone, lonazolac, lidocaine, ketoprofen, mefenamic acid, piroxicam, meloxicam, penicillamine, hydroxychloroquine, sodium aurothiomalate, oxaceprol, β-sitosterol, myrtecaine, polidocanol, nonivamide, levomenthol, ellipticine, N-(Pyridin-4-yl)-[1-(4-chlorobenzyl)-indol-3-yl]-glyoxyl amide, N-methy-N-deacetylcolcicine, cytochalasin A-E, indanocine, nocodazole, bacitracin, vitronectin receptor antagonists, azelastine, guanidyl cyclase stimulator, tissue inhibitor of metal proteinase-1 and 2, free nucleic acids, nucleic acids incorporated into virus transmitters, DNA and RNA fragments, plasminogen activator inhibitor 1, plasminogen activator inhibitor 2, antisense oligonucleotides, VEGF inhibitors, IGF-1, active agents from the group of antibiotics, cefadroxil, cefazolin, cefaclor, cefoxitin, tobramycin, gentamicin, penicillins, dicloxacillin, oxacillin, sulfonamides, metronidazole, enoxaparin, heparin, hirudin, PPACK, protamine, prourokinase, streptokinase, warfarin, urokinase, vasodilators, dipyramidole, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, halofuginone, nifedipine, tocopherol, tranilast, molsidomine, tea polyphenols, epicatechin gallate, epigallocatechin gallate, leflunomide, etanercept, sulfasalazine, tetracycline, triamcinolone, mutamycin, procainimide, retinoic acid, quinidine, disopyrimide, flecainide, propafenone, sotalol, natural and synthetically obtained steroids, bryophyllin A, inotodiol, maquiroside A, ghalakinoside, mansonine, strebloside, hydrocortisone, betamethasone, dexamethasone, non-steroidal substances, fenoprofen, ibuprofen, indomethacin, naproxen, phenylbutazone, antiviral agents, acyclovir, ganciclovir zidovudine, clotrimazole, flucytosine, griseofulvin, ketoconazole, miconazole, nystatin, terbinafine, antiprotozoal agents, chloroquine, mefloquine, quinine, natural terpenoids, hippocaesculin, barringtogenol-C21-angelate, 14-dehydroagrostistachin, agroskerin, agrostistachin, 17-hydroxyagrostistachin, ovatodiolids, 4,7-oxycycloanisomelic acid baccharinoids B 1, B2, B3 and B7, tubeimoside, bruceantinoside C, yadanziosides N and P, isodeoxyelephantopin, tomenphantopin A and B, coronarin A, B C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterine, protoanemonin, cheliburin chloride, sinococuline A and B, dihydronitidine, nitidine chloride, 12-β-hydroxypregnadien-3,20-dione, helenalin, indicine, indicine-N-oxide, lasiocarpine, inotodiol, podophyllotoxin, justicidin A and B, larreatin, malloterin, mallotochromanol, isobutyrylmallotochromanol, marchantin A, maytansin, lycoridicin, margetine, pancratistatin, liriodenine, oxoushinsunine, periplocoside A, deoxypsorospermin, psychorubin, ricin A, sanguinarine, manwu wheat acid, methylsorbifolin, chromones of spathelia, stizophyllin, dihydrousambaraensine, hydroxyusambarine, strychnopentamine, strychnophylline, usambarine, usambarensine, liriodenine, daphnoretin, lariciresinol, methoxylariciresinol, syringaresinol, sirolimus, somatostatin, tacrolimus, roxithromycin, troleandomycin, simvastatin, rosuvastatin, vinblastine, vincristine, vindesine, teniposide, vinorelbine, trofosfamide, treosulfan, temozolomide, thiotepa, tretinoin, spiramycin, umbelliferone, desacetylvismione A, vismione A and B, and zeorin.

\* \* \* \* \*